(12) United States Patent
Bomberger et al.

(10) Patent No.: US 6,991,727 B2
(45) Date of Patent: Jan. 31, 2006

(54) HOLLOW FIBER CONTACTOR SYSTEMS FOR REMOVAL OF LIPIDS FROM FLUIDS

(75) Inventors: David C. Bomberger, Belmont, CA (US); Pablo E. Garcia, Redwood City, CA (US); Eric Hegwer, Menlo Park, CA (US); Thomas P. Low, Belmont, CA (US); Ripudaman Malhotra, San Carlos, CA (US)

(73) Assignee: Lipid Sciences, Inc., Pleasanton, CA (US)

( * ) Notice: Subject to any disclaimer, the term of this patent is extended or adjusted under 35 U.S.C. 154(b) by 19 days.

(21) Appl. No.: 11/059,064

(22) Filed: Feb. 16, 2005

(65) Prior Publication Data

US 2005/0133450 A1  Jun. 23, 2005

Related U.S. Application Data

(63) Continuation of application No. 10/178,773, filed on Jun. 21, 2002, now abandoned.

(60) Provisional application No. 60/301,112, filed on Jun. 25, 2001, provisional application No. 60/301,108, filed on Jun. 25, 2001, provisional application No. 60/300,927, filed on Jun. 25, 2001, provisional application No. 60/301,109, filed on Jun. 25, 2001, provisional application No. 60/387,281, filed on Jun. 7, 2002.

(51) Int. Cl.
*B01D 11/04* (2006.01)
*A61M 37/00* (2006.01)

(52) U.S. Cl. ............................ 210/321.78; 210/321.79; 210/634; 210/645; 210/649; 210/790; 604/5.03; 422/256

(58) Field of Classification Search ................ 210/252, 210/253, 255, 257.2, 263, 321.79, 321.8, 210/645, 649, 660, 804–807; 604/5.03
See application file for complete search history.

(56) References Cited

U.S. PATENT DOCUMENTS 3,647,624 A    3/1972  Evenson (Continued)

FOREIGN PATENT DOCUMENTS

CA    1 271 708    7/1990

(Continued)

OTHER PUBLICATIONS

Agnese, et al., Clinical Biochemistry, Evaluation of Four Reagents for Delipidation of Serum, 16, 98-100. (1983).

(Continued)

*Primary Examiner*—W. L. Walker
*Assistant Examiner*—Krishnan S Menon
(74) *Attorney, Agent, or Firm*—Kilpatrick Stockton LLP

(57) ABSTRACT

This invention is directed to systems and methods for removing lipids from a fluid, such as plasma, or from lipid-containing organisms. These systems contact a fluid with an extraction solvent, which causes the lipids in the fluid to separate from the fluid or causes lipids in the lipid-containing organisms to separate from the lipid-containing organism, using at least one hollow fiber contactor. The separated lipids are removed from the fluid. The extraction solvent is removed from the fluid or at least reduced to a level below a particular threshold enabling the fluid to be administered to a patient without the patient experiencing undesirable consequences. Once the fluid has been processed, the fluid may be administered to a patient who donated the fluid, to a different patient, or be stored.

14 Claims, 5 Drawing Sheets

U.S. PATENT DOCUMENTS

| | | |
|---|---|---|
| 3,958,939 A | 5/1976 | Jones |
| 3,983,008 A | 9/1976 | Shinozaki et al. |
| 3,989,466 A | 11/1976 | Pan |
| 4,103,685 A | 8/1978 | Lupien et al. |
| 4,124,509 A | 11/1978 | Iijima et al. |
| 4,234,317 A | 11/1980 | Lucas et al. |
| 4,235,602 A | 11/1980 | Meyer et al. |
| 4,258,010 A | 3/1981 | Rozsa et al. |
| 4,350,156 A | 9/1982 | Malchesky et al. |
| 4,391,711 A | 7/1983 | Jackson et al. |
| 4,399,217 A | 8/1983 | Holmquist et al. |
| 4,402,940 A | 9/1983 | Nose et al. |
| 4,435,289 A * | 3/1984 | Breslau .................. 210/637 |
| 4,463,988 A | 8/1984 | Bouck et al. |
| 4,481,189 A | 11/1984 | Prince |
| 4,522,809 A | 6/1985 | Adamowicz et al. |
| 4,540,401 A | 9/1985 | Marten |
| 4,540,573 A | 9/1985 | Neurath et al. |
| 4,581,231 A | 4/1986 | Purcell et al. |
| 4,591,505 A | 5/1986 | Prince |
| 4,613,501 A | 9/1986 | Horowitz |
| 4,615,886 A | 10/1986 | Purcell et al. |
| 4,643,718 A | 2/1987 | Marten |
| 4,645,512 A | 2/1987 | Johns |
| 4,647,280 A | 3/1987 | Maaskant et al. |
| 4,648,974 A | 3/1987 | Rosskopf et al. |
| 4,668,398 A | 5/1987 | Silvis |
| 4,671,909 A | 6/1987 | Torobin |
| 4,676,905 A | 6/1987 | Nagao et al. |
| 4,677,057 A | 6/1987 | Curtiss et al. |
| 4,680,320 A | 7/1987 | Uku et al. |
| 4,696,670 A | 9/1987 | Ohnishi et al. |
| 4,775,483 A | 10/1988 | Mookerjea et al. |
| 4,832,034 A | 5/1989 | Pizziconi et al. |
| 4,836,928 A | 6/1989 | Aoyagi et al. |
| 4,879,037 A | 11/1989 | Utzinger |
| 4,895,558 A * | 1/1990 | Cham .................. 604/5.03 |
| 4,908,354 A | 3/1990 | Seidel et al. |
| 4,909,940 A | 3/1990 | Horowitz et al. |
| 4,909,942 A | 3/1990 | Sato et al. |
| 4,923,439 A | 5/1990 | Seidel et al. |
| 4,935,204 A | 6/1990 | Seidel et al. |
| 4,966,709 A | 10/1990 | Nose et al. |
| 4,970,144 A | 11/1990 | Fareed et al. |
| 5,026,479 A | 6/1991 | Bikson et al. |
| 5,080,796 A | 1/1992 | Nose et al. |
| 5,089,602 A | 2/1992 | Isliker et al. |
| 5,112,956 A | 5/1992 | Tang et al. |
| 5,116,307 A | 5/1992 | Collins |
| 5,126,240 A | 6/1992 | Curtiss |
| 5,128,318 A | 7/1992 | Levine et al. |
| 5,152,743 A | 10/1992 | Gorsuch et al. |
| 5,187,010 A | 2/1993 | Parham et al. |
| 5,203,778 A | 4/1993 | Boehringer et al. |
| 5,211,850 A | 5/1993 | Shettigar et al. |
| 5,236,644 A | 8/1993 | Parham et al. |
| 5,256,767 A | 10/1993 | Salk et al. |
| 5,258,149 A | 11/1993 | Parham et al. |
| 5,279,540 A | 1/1994 | Davidson |
| 5,301,694 A | 4/1994 | Raymond et al. |
| 5,354,262 A | 10/1994 | Boehringer et al. |
| 5,391,143 A | 2/1995 | Kensey |
| 5,393,429 A | 2/1995 | Nakayama et al. |
| 5,401,415 A | 3/1995 | Rauh et al. |
| 5,401,466 A | 3/1995 | Foltz et al. |
| 5,418,061 A | 5/1995 | Parham et al. |
| 5,419,759 A | 5/1995 | Naficy |
| 5,424,068 A | 6/1995 | Filip |
| 5,476,715 A | 12/1995 | Otto |
| 5,484,396 A | 1/1996 | Naficy |
| 5,496,637 A | 3/1996 | Parham et al. |
| 5,523,096 A | 6/1996 | Okarma et al. |
| 5,634,893 A | 6/1997 | Rishton |
| 5,637,224 A | 6/1997 | Sirkar et al. |
| 5,652,339 A | 7/1997 | Lerch et al. |
| 5,679,260 A | 10/1997 | Boos et al. |
| 5,698,432 A | 12/1997 | Oxford |
| 5,707,673 A | 1/1998 | Prevost et al. |
| 5,719,194 A | 2/1998 | Mann et al. |
| 5,744,038 A | 4/1998 | Cham |
| 5,753,227 A | 5/1998 | Strahilevitz |
| 5,853,725 A | 12/1998 | Salk et al. |
| 5,855,782 A | 1/1999 | Falkenhagen et al. |
| 5,858,238 A * | 1/1999 | McRea et al. .............. 210/645 |
| 5,877,005 A | 3/1999 | Castor |
| 5,885,578 A | 3/1999 | Salk et al. |
| 5,895,650 A | 4/1999 | Salk et al. |
| 5,911,698 A | 6/1999 | Cham |
| 5,916,806 A | 6/1999 | Salk et al. |
| 5,919,369 A | 7/1999 | Ash |
| 5,928,930 A | 7/1999 | Salk et al. |
| 5,948,441 A | 9/1999 | Lenk et al. |
| 5,962,322 A | 10/1999 | Kozarsky et al. |
| 5,980,478 A | 11/1999 | Gorsuch et al. |
| 6,004,925 A | 12/1999 | Dasseux et al. |
| 6,017,543 A | 1/2000 | Salk et al. |
| 6,022,333 A | 2/2000 | Kensey |
| 6,037,323 A | 3/2000 | Dasseux et al. |
| 6,037,458 A | 3/2000 | Hirai et al. |
| 6,039,946 A | 3/2000 | Strahilevitz |
| 6,046,166 A | 4/2000 | Dasseux et al. |
| 6,080,778 A | 6/2000 | Yankner et al. |
| 6,127,370 A | 10/2000 | Smith et al. |
| 6,136,321 A | 10/2000 | Barrett et al. |
| 6,139,746 A | 10/2000 | Kopf |
| 6,156,727 A | 12/2000 | Garber et al. |
| 6,171,373 B1 | 1/2001 | Park et al. |
| 6,193,891 B1 | 2/2001 | Kent et al. |
| 6,264,623 B1 | 7/2001 | Strahilevitz |
| 6,309,550 B1 | 10/2001 | Iversen et al. |
| 6,337,368 B1 | 1/2002 | Kobayashi et al. |
| 6,440,387 B1 | 8/2002 | Yankner et al. |
| 6,472,421 B1 | 10/2002 | Wolozin |
| 6,605,588 B1 | 8/2003 | Lees et al. |
| 6,706,008 B2 | 3/2004 | Vishnoi et al. |
| 2001/0028895 A1 | 10/2001 | Bisgaier et al. |
| 2002/0055529 A1 | 5/2002 | Bisgaier et al. |
| 2002/0081263 A1 | 6/2002 | Yankner et al. |
| 2002/0107173 A1 | 8/2002 | Friedhoff et al. |
| 2002/0183379 A1 | 12/2002 | Yankner et al. |
| 2002/0188012 A1 | 12/2002 | Bisgaier et al. |
| 2003/0018013 A1 | 1/2003 | Dasseux |

FOREIGN PATENT DOCUMENTS

| | | |
|---|---|---|
| CN | 1189378 | 8/1998 |
| DE | 29 44 138 A1 | 6/1981 |
| DE | 31 18 072 A1 | 11/1982 |
| DE | 32 13 390 A1 | 10/1983 |
| DE | 33 10 263 A1 | 9/1984 |
| EP | 0 036 283 A2 | 9/1981 |
| EP | 0 267 471 A1 | 5/1988 |
| FR | 2 571 971 A1 | 4/1986 |
| GB | 1183506 | 3/1970 |
| JP | 127104 | 1/1980 |
| JP | 277303 | 10/1993 |
| SU | 1116396 A | 9/1984 |
| SU | 1204224 A | 1/1986 |
| SU | 1752187 A3 | 7/1992 |
| WO | WO 88/09345 A1 | 12/1988 |
| WO | WO 95/03840 A1 | 2/1995 |
| WO | WO 99/38498 A1 | 8/1999 |
| WO | WO 01/45718 A1 | 6/2001 |
| WO | WO 01/56579 A1 | 8/2001 |

| | | | |
|---|---|---|---|
| WO | WO 02/010768 A3 | 2/2002 |
| WO | WO 02/30863 A2 | 4/2002 |
| WO | WO 02/062824 A2 | 8/2002 |
| WO | PCT/US02/19722 | 10/2002 |

OTHER PUBLICATIONS

Albouz, et al., Ann. Biol. Clin., Extraction of Plasma Lipids Preserving Antigenic Properties of Proteins and Allowing Quantitation of Gangliosides by Neuraminic Acid Determination, 37, 287-290. (abstract only) (1979).

Andre et al., Journal of Virology, Characterization of Low- and Very-Low-Density Hepatitis C Virus RNA-Containing Particles, 76 (14), 6919-6928. (Jul. 2002).

Asztalos et al., Arterioscler. Thromb. Vasc. Biol., Distribution of Apo A-1-Containing HDL Subpopulations in Patients with Coronary Heart Disease, 2670-2676. (Dec. 1, 2000).

Asztalos et al., Arterioscler. Thromb. Vasc. Biol., Presence and Formation of Free Apollpoprotein A-l-Lixe' Particles in Human Plasma, 15, 1419-1423. (1995).

Asztalos et al., Arterioscler. Thromb. Vasc. Biol., Role of Free Apollpoprotein A-l in Cholosterol Efflux, 17, 1630-1636. (1997).

Badimon, et al., Laboratory Investigation, High Density Lipoprotein Plasma Fractions Inhibit Aortic Fatty Streaks in Cholesterol-Fed Rabbits, 60, 455-461. (1989).

Badimon, et al., J. Clinical Investigation, Regression of Atherosclerotic Lesions by High Density Lipoprotein Plasma Fraction in the Cholesterol-Fed Rabbit, 85, 1234-1241. (1990).

Barrans et al., Biochimica et Biophysica Acta, Pre-β HDL: Structure and Metabolism, 1300, 73-85. (1996).

Barres et al., Science, Cholesterol—Making or Breaking the Synapse, 294, 1296/1297. (Nov. 9, 2001).

Bloom, et al., Clin. Biochem., Quantitation of lipid profiles from isolated serum lipoproteins using small volumes of human serum, 14, 119-125, (abstract only) (Jun. 1981).

Burns et al., Neurochem Res, Use of In Vivo Models to Study the Role of Cholesterol in the Etiology of Alzheimer's Disease 28, 979-86. (abstract only) (Jul. 2003).

Cham, Clinical Chemistry, Nature of the Interaction Between Low-Density Lipoproteins and Polyanions and Metal Ions, as Examplified by Heparin and $Ca^{2+}$, 22, 1812-1816. (1976).

Cham, et al., J. of Lipid Research, A Solvent Systems for Delipidation of Plasma or Serum Without Protein Precipitation, 17, 176-181. (1976).

Cham, et al., Clinical Chemistry, Changes in Electrophoretic Mobilities of α- and β-Lipoproteins as a Result of Plasma Delipidation, 22, 305-309. (1976).

Cham, et al., Biochemical and Biophysical Research Communications, Heterogenelty of Lipoprotein B, 103, 196-206. (1981).

Cham, et al., Chem. Biol. Interactions, Importance of Apolipoproteins in Lipid Metabolism, 20, 263-277, (1978).

Cham, et al., J. Biol. Chem., In Vitro Partial Relipidation of Apolipoproteins in Plasma, 251, 6367-6371, (abstract only) (1976).

Cham, et al., Pharmacol. (Life Sci. Adv.), Lipid Apheresis in an Animal Model Causes Acute Reduction in plasma Lipid Concentrations and Mobilisation of Lipid from Liver and Aorta, 13, 25-32. (1994).

Cham, et al., J. Clin. Apheresis, Lipid Apheresis in an Animal Model Causes In Vivo Changes in Lipoprotein Electrophoretic Patterns, 11, 61-70, (1996).

Cham, et al., J. Clin. Apheresis, Lipid Apheresis: An In Vivo Application of Plasma Delipidation with Organic Solvents Resulting in Acute Transient Reduction of Circulating Plasma Lipids in Animals, 10, 61-69. (1995).

Cham, et al., Clinical Chemistry, Phospholipids in EDTA—Treated Plasma and Serum, 39, 2347-2348. (1993).

Cham, et al., 59th Congress European Altherosclerosis Society, Nice, France, Rapid Regression of Atherosclerosis by Cholesterol Apheresis—A Newly Developed Technique, 17-21. (abstract only) (May 1992).

Cham, et al., Clinical Chimica Acta, Rapid, Sensitive Method for the Separation of Free Cholesterol from Ester Cholesterol, 49, 109-113. (1973).

Collet et al., Journal of Biological Chemistry, Differential Effects of Lecithin and Cholesterol on the Immunoreactivity and Confirmation of Apolipoprotein A-l in High Density Lipoproteins, 266 (14), 9145-9152, (May 15, 1991).

Cooper, Drugs Aging, Dietary Lipids in the Aetiology of Alzheimer's Disease: Implications for Therapy, 20 (6), 399-418. (abstract only) (2003).

Cruzado et al., Analytical Biochemistry, Characterization and Quantitation of the Apoproteins of High-Density Lipoprotein by Capillary Electrophoresis, 14 (7), 100-109. (1996).

Dass, C.R., Apolipoprotein A-1, Phospholipid Vesicies, and Cyclodextrins as Potential Anti-Atherosclerotic Drugs: Delivery, Pharmacokinetics, and Efficacy, Drug Deliv. 2000 Jul.-Sep.; 7(3):161-82.

Deva, et al., J. Hosp. Infect., Establishment of an in-use testing method for evaluating disinfection of surgical instruments using the duck hepatitis B model, 22, 119-130. (abstract only) (Jun. 1996).

Dwlvedy, 18th Australian Atherosclerosis Society Conference, Surfers Paradise, Increase of Reverse Cholesterol Transport by Cholesterol Apheresis Regression of Atherosclerosis, 21. (1992).

Eisenhauer, et al, Klin Wochenschr (KWH), Selective Removal of Low Density Lipoproteins (LDL) by Precipitation at Low pH: First Clinical Application of the HELP System, 65, 161-168. (1987).

Fang, et al., 18th Australian Atherosclerosis Society Conference, Gold coast, Australia, In Vivo Rapid Mobilization of Adipose Tissue by Lipid Apheresis—A Newly Developed Technique. (1992).

Feinberg, et al. AIDS Vaccine Models: Challenging Challenge Viruses, nature Medicine, Mar. 2002, 8(3): 207-210.

Feinstone, et al., Infection and Immunity, Inactivation of Hepatits B Virus and Non-A, Non-B Hepatitis by Chloroform, 41, 816-821. (Aug. 1983).

Golde et al., Drug Discovery Today, Cholesterol Modulation as an Emerging Strategy for the Treatment of Alzheimer's Disease, 6 (20), 1049-1055. (abstract only) (Oct. 15, 2001).

Hatch et al., Lipoprotein Analysis, Advances in Lipid Research, Practical methods for Plasma Lipoprotein Analysis, 6, 1-68. (1968).

Horowitz, et al., Blood Coagulation and Fibrinolysis, Viral Safety of solvent/detergent-treated blood products, 5, S21-S28. (1994).

Innerarity, et al., Biochemistry, Enhanced Binding by Cultured Human Fibroblasts of Apo-E-Containing Lipoproteins as Compared with Low Density Lipoproteins, 17, 1440-1447. (1978).

Ito J., Nagayasu Y. et al. Cholesterol-Sphingomyelin Interaction in Membrane and Apolipoprotein-Mediated Cellular Cholesterol Efflux, J Lipid Res., Jun. 2000; 41(6): 894-904.

Jackson et al., Biochimica et Biophysics Acta, Isolation and Characterization of the Major Apollpoprotein from Chicken High Density Lipoproteins, 420, 342-349. (1976).

Klimov, et al., Kardologiia, Extraction of Lipids from Blood Plasma and Subsequent Introduction of Autologous Delipidized Plasma into the Body as a Possible Means to Treat Altherosclerosis [translation], 18, 23-29. (1978).

Koizumi, et al., J. Lipid Research, Behavior of Human Apolipoprotein A-1: Phospho-Lipid and apoHDL: Phospholipid Complexes In Vitro and After Injection into Rabbits, 29, 1405-1415. (1988).

Kostner, et al., XI Internet Symp. on Drugs Affecting Lipid Metabolism, Italy, Increase of APO A1 Concentration in Hypercholesteraemic Chickens after Treatment with a newly Developed Extracorpreal Lipid Elimination. (May 13, 1992).

Kostner, et al., European Journal of Clinical Investigation, Lecithin-cholesterol acyltransferase activity in Normocholesterolaemic and Hypercholesterolaemic Roosters: Modulation by Lipid Apheresis, 27, 212-218. (May 7, 1997).

Koudinov et al., Clin Chim Acta, Alzheimer's Amyloid Beta Interaction with Normal Human Plasma High Density Lipoprotein: Association with Apolipoprotein and Lipids, 270 (2), 75-84. (abstract only) (Feb. 23, 1999).

Koudinov et al., Cell Biol Int., Alzheimer's Soluble Amyloid Beta Protein Is Secreted by HepG2 Cells as an Apolipoprotein, 21 (5), 265-71. (abstract only) (May 1997).

Koudinov et al., Biochem Biophys Res Commun, Biochemical Characterization of Alzheimer's Soluble Amyloid Beta Protein in Human Cerebrospinal Fluid: Association with High Density Lipoproteins 223 (3), 592-7. (abstract only) (Jun. 25, 1999).

Koudinov et al., Science, Cholesterol's Role in Synapse Formation, 294, 2213. (Nov. 9, 2001).

Koudinova et al., Soc. Neuroscience Abstract Viewer and Itinerary Planner, Amyloid Beta, Neural Lipids, Cholesterol and Alzheimer's Disease—Abstract No, 21.10. (2002).

Lipid Sciences, http://www.lipidsciences.com/technology.html, Lipid Technology, 1-4. (Aug. 25, 2001).

Luplen, et al., Lancet (LOS), A New Approach to the Management of Familial Hypercholesterolaemia: Removal of Plasma-Cholesterol Based on the Principle of Affinity Chromatography, 1, 1261-1265. (1976).

Mauch et al., Science, CNS Synaplogenesis Promoted by Glia-Derived Cholesterol, 294, 1354-1357. (Nov. 9, 2001).

Moya et al., Arterisclerosis and Thrombosis, A Cell Culture System for Screening Human Serum for Ability to Promote Cellular Cholesterol Efflux, 14 (7), 1056-1065. (Jul. 1994).

Ngu, Medical Hypotheses, Chronic Infections from the Perspective of Evolution: a Hypothesis, 42, 61-68. (1994).

Ngu, Medical Hypotheses, Human Cancers and Viruses: A Hypothesis for Immune Destruction of Tumours Caused by Certain Enveloped Viruses Using Modified Viral Antigens, 39, 17-21. (1992).

Ngu, Medical Hypotheses, The viral envelope in the evolution of HIV: a hypothetical approach to inducing an effective immune response to the virus, 48, 517-521. (1997).

Okazaki et al., Journal of Chromatography, Biomedical Applications, Improved High-Performance Liquid Chromatographic Method for the Determination of Apolopoproteins in Serum High-Density Lipoproteins, 430, 135-142. (1988).

Parker, et al., Proceedings of the National Academy of Sciences, Plasma High Density Lipoprotein is Increased in Man When Low Density Lipoprotein (LDL) is Lowered by LDL-Pheresis, 83, 777-781. (1986).

Patemo et al., Department of Clinical and Experimental Medicine, Reconstituted High-Density Lipoprotein Exhibits Neuroprotection in Two Rat Models of Stroke. (Abstract only) (Dec. 29, 2003).

Refolo et al., Soc. Neuroscience Abstracts. Cholesterol Metabolism: A Potential Target for Alzheimer's Disease Therapy, 27 (2), 1518. (abstract only) (2001).

Robern et al., Experientia, The Application of Sodium Deoxycholate and Sephacryl-200 for the Delipidation and Separation of High Density Lipoproteins, 38, 437-439. (1982).

Ryan, et al., Clinical Chemistry, An Improved Extraction Procedure for the Determination of Triglycerides and Cholesterol in Plasma or Serum, 13, 769-772. (1967).

Seanu et al., Analytical Biochemistry, Solubility in Aqueous Solutions of Ethanol of the Small Molecular Weight Peptides of the Serum Very Low Density and High Density Lipoproteins: Relevance to the Recovery Problem During Delipidation of Serum Lipoproteins, 44, 576-588. (1971).

Segrasi et al., Journal of Biological Chemistry, A Detailed Molecular Bell Model for Apollpoprotein A-l in Discoidal High Density Lipoprotein, 274 (45), 31755-31758. (Nov. 5, 1999).

Slater, et al., J. of Lipid Research, A Comparison of Delipidated Sera Used in Studies of Sterol Synthesis by Human Mononuclear Leukocytes, 20, 413-416. (1979).

Slater, et al., Atherosclerosis, The Effect of Delipidated High Density Lipoprotein on Human Leukocyte Sterol Synthesis, 35, 41-49, (1960).

Thompson, et al., Lancet (LOS), Plasma Exchange in the Management of Homozygous Familial Hypercholesterolaernia, 1, 1208-1211. (1975).

Tricerri, M.A. et al., Interaction of Apoilpoprotein A-1 in Three Different Conformations with Palmiloly Oleoyl Phosphatidyicholine Vesicies, J Lipid Res. 2002; 43(2): 187-97.

Williams, et al., Proc. Natl. Acad. Sci. USA, Low Density Lipoprotein Receptor-Independent Hepatic Uptake of a Synthetic, Cholesterol-Scavenging Lipoprotein: Implications for the Treatment of Receptor-Deficient Atherosclerosis, 85, 242-246. (1988).

Williams et al., Biochim. Biophys. Act., Uptake of Endogenous Cholesterol by a Synthetic Lipoprotein, 875 (2), 183-194. (Feb. 23, 1986).

Wong, et al, Journal of Lipid Research, Retention of gangliosides in serum delipidated by diisopropyl ether-1-butanol extraction, 24, 666-669. (1983).

Wormser, Henry, PSC3110—Fall Semester 2002, Lipids.

Yokoyama, et al., Artheriosclerosis, Selective Removal of Low Density Lipoprotein by Plasmapheresis in Familial Hypercholesterolemia, 5, 613-622, (1985).

Yoshidome et al., Artif Organs, Serum Amyloid A and P Protein Levels are Lowered by Dextran Sulfate Cellulose Low-Density Lipoprotein Apheresis, 22 (2), 144-148. (1998).

Zetia, http://www.zetia.com/ezetimbe/zetia/hcp/product_highlights/index./sp. Zelia (ezetimibe), 1-2. (Jul. 16, 2003).

Zetia, http://www.zetia.com/ezetimibe/zetia.hcp/mechanism_of_action/index.jsp, Zetia: Compliments Statin with a Unique Mechanism, 1-2. (Jul. 18, 2003).

Zhang et al., Journal of Lipid Research, Characterization of phospholipids in a pre-alpha HDL: Selective Phospholipid Efflux with Apolipoprotein A-1, 29, 1601-1607. (1998).

* cited by examiner

HOLLOW FIBER CONTACTOR SYSTEMS FOR REMOVAL OF LIPIDS FROM FLUIDS

RELATED APPLICATIONS

This application is a continuation application of U.S. application Ser. No. 10/178,773, filed Jun. 21, 2002, now abandoned which claims priority to each of the following U.S. provisional patent applications: U.S. Provisional Patent Application No. 60/301,112, filed Jun. 25, 2001; U.S. Provisional Patent Application No. 60/301,108, filed Jun. 25, 2001; U.S. Provisional Patent Application No. 60/300,927, filed Jun. 25, 2001; U.S. Provisional Patent Application No. 60/301,109, filed Jun. 25, 2001; and U.S. Provisional Patent Application No. 60/387,281, filed Jun. 7, 2002; the entire contents of each of the above-listed applications being incorporated by reference herein.

FIELD OF THE INVENTION

The present invention relates to systems and methods for the removal of lipids from fluids, especially plasma, or from lipid-containing organisms, or both, using solvent extraction. The delipidated fluid may be administered to an animal or human for therapeutic use such as treatment of arteriosclerosis and atherosclerotic vascular diseases, removal of excess fat within an animal or human, and reduction of infectivity of lipid-containing organisms.

BACKGROUND OF THE INVENTION

Hyperlipidemia and Arteriosclerosis

Cardiovascular, cerebrovascular, and peripheral vascular diseases are responsible for a significant number of deaths annually in many industrialized countries. One of the most common pathological processes underlying these diseases is arteriosclerosis. Arteriosclerosis is characterized by lesions, which begin as localized fatty thickenings in the inner aspects of blood vessels supplying blood to the heart, brain, and other organs and tissues throughout the body. Over time, these atherosclerotic lesions may ulcerate, exposing fatty plaque deposits that may break away and embolize within the circulation. Atherosclerotic lesions obstruct the lumens of the affected blood vessels and often reduce the blood flow within the blood vessels, which may result in ischemia of the tissue supplied by the blood vessel. Embolization of atherosclerotic plaques may produce acute obstruction and ischemia in distal blood vessels. Such ischemia, whether prolonged or acute, may result in a heart attack or stroke from which the patient may or may not recover. Similar ischemia in an artery supplying an extremity may result in gangrene requiring amputation of the extremity.

For some time, the medical community has recognized the relationship between arteriosclerosis and levels of dietary lipid, serum cholesterol, and serum triglycerides within a patient's blood stream. Many epidemiological studies have been conducted revealing that the amount of serum cholesterol within a patient's blood is a significant predictor of coronary disease. Similarly, the medical community has recognized the relationship between hyperlipidemia and insulin resistance, which can lead to diabetes mellitus. Further, hyperlipidemia and arteriosclerosis have been identified as being related to other major health problems, such as obesity and hypertension. Hyperlipidemia may be treated by changing a patient's diet. However, use of a patient's diet as a primary mode of therapy requires a major effort on the part of patients, physicians, nutritionists, dietitians, and other health care professionals and thus undesirably taxes the resources of health professionals. Another negative aspect of this therapy is that its success does not rest exclusively on diet. Rather, success of dietary therapy depends upon a combination of social, psychological, economic, and behavioral factors. Thus, therapy based only on correcting flaws within a patient's diet is not always successful.

In instances when dietary modification has been unsuccessful, drug therapy has been used as an alternative. Such therapy has included use of commercially available hypolipidemic drugs administered alone or in combination with other therapies as a supplement to dietary control. Hypolipidemic drugs have had varying degrees of success in reducing blood lipid; however, none of the hypolipidemic drugs successfully treats all types of hyperlipidemia. While some hypolipidemic drugs have been fairly successful, the medical community has not found any conclusive evidence that hypolipidemic drugs cause regression of atherosclerosis. In addition, all hypolipidemic drugs have undesirable side effects. As a result of the lack of success of dietary control, drug therapy and other therapies, atherosclerosis remains a major cause of death in many parts of the world.

To combat this disturbing fact, a relatively new therapy has been used to reduce the amount of lipid in patients for whom drug and diet therapies were not sufficiently effective. This therapy, referred to as plasmapheresis therapy or plasma exchange therapy, involves replacing a patient's plasma with donor plasma or more usually a plasma protein fraction. While having been fairly successful, this treatment has resulted in complications due to introduction of foreign proteins and transmission of infectious diseases. Further, plasma exchange undesirably removes many plasma proteins, such as very low-density lipoprotein (VLDL), low-density lipoprotein (LDL), and high-density lipoprotein (HDL).

HDL is secreted from both the liver and the intestine as nascent, disk-shaped particles that contain cholesterol and phospholipids. HDL is believed to play a role in reverse cholesterol transport, which is the process by which excess cholesterol is removed from tissues and transported to the liver for reuse or disposal in the bile. Therefore, removal of HDL from plasma is not desirable.

Other apheresis techniques exist that can remove LDL from plasma. These techniques include absorption of LDL in heparin-agarose beads (affinity chromatography), the use of immobilized LDL-antibodies, cascade filtration absorption to immobilize dextran sulphate, and LDL precipitation at low pH in the presence of heparin. Each method removes LDL but not HDL.

LDL apheresis, however, has disadvantages. For instance, significant amounts of plasma proteins in addition to LDL are removed during apheresis. In addition, LDL apheresis must be performed frequently, such as weekly, to obtain a sustained reduction in LDL-cholesterol. Furthermore, LDL removal may be counterproductive because low LDL levels in a patient's blood may result in increased cellular cholesterol synthesis. Thus, removal of LDL from a patient's blood may have negative side effects.

Yet another method of achieving a reduction in plasma cholesterol in homozygous familial hypercholesterolemia, heterozygous familial hypercholesterolemia and patients with acquired hyperlipidemia is an extracorporeal lipid elimination process, referred to as cholesterol apheresis. In cholesterol apheresis, blood is withdrawn from a patient, the plasma is separated from the blood, and the plasma is mixed with a solvent mixture. The solvent mixture extracts lipids from the plasma. Thereafter, the delipidated plasma is recombined with the patient's blood cells and returned to the patient.

More specifically, lipid apheresis results in the removal of fats from plasma or serum. However, unlike LDL apheresis, the proteins (apolipoproteins) that transport lipids remain soluble in the treated plasma or serum. Thus, the apolipoproteins of VLDL, LDL and HDL are present in the treated plasma or serum. These apolipoproteins, in particular apolipoprotein A1 from the delipidated HDL in the plasma or serum, are responsible for the mobilization of unwanted lipids or toxins, such as excessive amounts of deposited lipids including cholesterol in arteries, plaques, and excessive amounts of triglycerides, adipose tissue, and fat soluble toxins present in adipose tissue. These excessive amounts of lipids or toxins are transferred to the plasma or serum, and then bound to the newly assembled apolipoproteins. Application of another lipid apheresis procedure successively removes these unwanted lipids or toxins from the plasma and thus the body. The main advantage of this procedure is that LDL and HDL are not removed from the plasma. Instead, only cholesterol, some phospholipid and a considerable amount of triglycerides are removed.

While lipid apheresis has the potential to overcome the shortcomings of dietary control, drug therapy and other apheresis techniques, existing apparatuses and methods for lipid apheresis do not provide a sufficiently rapid and safe process. Thus, a need exists for systems, apparatuses and methods capable of conducting lipid apheresis more quickly than accomplished with conventional equipment and methods.

Unfortunately, existing lipid apheresis systems suffer from a number of disadvantages that limit their ability to be used in clinical applications, such as in doctors' offices and other medical facilities. One disadvantage is the explosive nature of the solvents used to delipidate this plasma. If used in a continuous system, these solvents are in close proximity to patients and medical staff. Thus, it would be advantageous to limit this exposure; however, this hazard is clearly present for the duration of the delipidation process, which usually runs for several hours.

Another disadvantage is the difficulty in removing a sufficient amount of solvents from the delipidated plasma in order for the delipidated plasma to be safely returned to a patient. In addition, patients are subjected to an increased chance of prolonged exposure to solvents in a continuous system. Furthermore, current techniques do not provide for sequential multi-washes because the volume of blood necessary for continuous processing using conventional equipment requires removal of an amount of blood that would harm the patient. In other words, conventional equipment does not allow for automated continuous removal, processing and return of plasma to a patient in a manner that does not negatively impact total blood volume of the patient. While the long-term toxicity of various extraction solvents is not known, especially when present in the bloodstream, clinicians know that some solvents may cross the blood-brain barrier. Furthermore, external contact with solvents is known to cause clinical symptoms, such as irritation of mucous membranes, contact dermatitis, headaches, dizziness and drowsiness. Therefore, conventional equipment for lipid apheresis is not adequate to conduct continuous processing of a patient's blood.

Infectious Disease

While the medical community has struggled to develop cures for hyperlipidemia and arteriosclerosis, it has likewise struggled in its battle against infectious diseases. Infectious diseases are a major cause of suffering and death throughout the world. Infectious disease of varied etiology affects billions of animals and humans each year and inflicts an enormous economic burden on society. Many infectious organisms contain lipid as a major component of the membrane that surrounds them. Three major classes of organisms that produce infectious disease and contain lipid in their cell wall or envelope include bacteria, viruses, and protozoa. Numerous bacteria and viruses that affect animals and humans cause extreme suffering, morbidity and mortality. Many bacteria and viruses travel throughout the body in fluids, such as blood, and some reside in plasma. These and other infectious agents may be found in other fluids, such as peritoneal fluid, lymphatic fluid, pleural fluid, pericardial fluid, cerebrospinal fluid, and in various fluids of the reproductive system. Disease can be caused at any site bathed by these fluids. Other bacteria and viruses reside primarily in different organ systems or in specific tissues, where they proliferate and enter the circulatory system to gain access to other tissues and organs.

Infectious agents, such as viruses, affect billions of people annually. Recent epidemics include the disease commonly known as acquired immune deficiency syndrome (AIDS), which is believed to be caused by the human immunodeficiency virus (HIV). This virus is rapidly spreading throughout the world and is prevalent in various sub-populations, including individuals who receive blood transfusions, individuals who use needles contaminated with the disease, and individuals who contact infected fluids. This disease is also widespread in certain countries. Currently, no known cure exists.

It has long been recognized that a simple, reliable and economically efficient method for reducing the infectivity of the HIV virus is needed to decrease transmission of the disease. Additionally, a method of treating fluids of infected individuals is needed to decrease transmission of the virus to others in contact with these fluids. Furthermore, a method of treating blood given to blood banks is needed to decrease transmission of the virus to individuals receiving transfusions. Moreover, an apparatus and method are needed for decreasing the viral load of an individual or an animal by treating the plasma of that individual and returning the treated plasma to the individual such that the viral load in the plasma is decreased.

Other major viral infections that affect animals and humans include, but are not limited to meningitis, cytomegalovirus, and hepatitis in its various forms. While some forms of hepatitis may be treated with drugs, other forms have not been successfully treated in the past.

At the present time, most anti-viral therapies focus on preventing or inhibiting viral replication by manipulating the initial attachment of the virus to the T4 lymphocyte or macrophage, the transcription of viral RNA to viral DNA and the assembly of new virus during reproduction. Such a focus has created major difficulty with existing treatments, especially with regard to HIV. Specifically, the high mutation rate of the HIV virus often renders treatments ineffective shortly after application. In addition, many different strains of HIV have already become or are becoming resistant to anti-viral drug therapy. Furthermore, during anti-viral therapy, resistant strains of the virus may evolve. Finally, many common therapies for HIV infection involve several undesirable side effects and require patients to ingest numerous pills daily. Unfortunately, many individuals are afflicted with multiple infections caused by more than one infectious agent, such as HIV, hepatitis and tuberculosis. Such individuals require even more aggressive and expensive drugs to counteract disease progression. Such drugs may cause numerous side effects as well as multi-drug resistance. Therefore, an effective method and apparatus is needed that does not rely on drugs for combating infections organisms found in fluids. Such a method should reduce the infectivity of infectious organisms.

Thus, a need exists to overcome the deficiencies of conventional systems and methods for removing lipids from fluids, such as plasma or serum, and for removing lipids from infectious organisms contained in a fluid. Furthermore, a need exists for an apparatus and method to perform delipidation rapidly, either in a continuous or discontinuous manner of operation. A need further exists for such an apparatus and process to perform safely and reliably, and to produce delipidated fluid having residual plasma solvent levels meeting acceptable standards. In addition, a need exists for an apparatus having minimal physical connection between a patient and the lipid apheresis process. Furthermore, a need exists for an economical medical apparatus that is sterile and made of a disposable construction for a single use application. Finally, a need exists for such an apparatus and process to be automated, thereby requiring minimal operator intervention during the course of normal operation.

SUMMARY OF THE INVENTION

This invention is directed to systems and methods for removing lipids from a liquid, and more particularly, this invention is directed to the removal of lipids from plasma or from lipid-containing organisms using devices employing multiple solvents. Specifically, the system is adapted to remove lipids from a fluid after passing through the system only once.

According to one embodiment, the system for removal of lipids from fluids or from lipid-containing organisms, or both, typically includes three subsystems, which may include, but are not limited to, an initial phase subsystem, an intermediate phase subsystem, and a final phase subsystem. The initial phase subsystem is composed in part of a fluid source, a first extraction solvent source, and a device, such as a hollow fiber contactor (HFC), for combining the biological source and the first extraction solvent.

The HFC is composed of a generally hollow cylindrical body, referred to as the shell, having a plurality of hollow fibers that are positioned in the body generally parallel to a longitudinal axis of the body. Each hollow fiber has a length slightly shorter than the length of the body of the HFC and has a very small diameter. A HFC typically has about 3,000 to about 5,000 hollow fibers positioned within its body, but may have as few as two or three hollow fibers or greater than 5,000 hollow fibers. An HFC is primarily defined by several characteristics: the type of membrane material of the hollow fiber, the type and number of holes or pores in the membrane of the hollow fiber, the size of the pores, and the total effective surface area of the fibers or membrane. The HFC also contains chambers at each end to feed a fluid or gas into the hollow fibers at one end and receive the fluid or gas at the other end of the hollow fibers. The HFC allows another fluid or gas to flow around the outside of the hollow fibers in a region referred to as a chamber or the shell side of the hollow fibers. The chamber is formed by the interior surface of the shell forming the HFC and the outside surfaces of the hollow fibers.

For purposes of this invention, the fluid containing lipids or lipid-containing organisms flows through the lumens of the hollow fibers while simultaneously, the first extraction solvent flows through the chamber on the shell side of the hollow fibers, or vice versa. The fluid is directed through the lumens of the hollow fibers because the volume of the lumens is less than the shell side of the lumens; therefore, keeping the volume fluids withdrawn from a patient to a minimum. The first extraction solvents permeate the hollow fibers and mix with the fluids within the lumens of the hollow fibers. The first extraction solvent produces a suspension of lipid particles in the first mixture that is formed from a fluid and the first extraction solvent. The solvent disrupts the lipid-protein structure and frees the lipid particles, which are not very soluble in the fluid.

A substantial amount of lipid is removed from the fluid due to a diffusion gradient established between the high concentration of lipid in the fluid in the hollow fibers and the zero or low concentration of lipid in the extraction solvent located on the shell side of the hollow fibers. The lipids dissolve in the solvents, diffuse through the membranes forming the hollow fibers, and are carried away by the extraction solvent in the shell. Some of the lipids may also attach to the surface of the hollow fibers. Further, some lipid particles may be removed with a filter positioned between the initial phase subsystem and the final phase subsystem. The concentration of lipids in the fluid after passing through the first phase subsystem is less than the initial concentration of lipids in the fluid prior to starting the process. The first phase subsystem forms a first mixture of fluid containing lipids or lipid containing organisms, or both, and first extraction solvent. The first extraction solvent contained in the HFC on the shell side of the hollow fibers in the first subsystem is removed and may be discarded as waste. After passing through the first phase subsystem, the fluid is immediately passed to the intermediate phase subsystem.

In the intermediate phase subsystem, the first mixture received from the initial phase subsystem is sent through at least one HFC. The HFC may be similar or different than the HFC used in the initial phase subsystem. More specifically, the mixture is sent through the hollow fibers of the HFC and contacted with a second separate extraction solvent that is contained in the HFC on the shell side of the hollow fibers, or vice versa. The second extraction solvent primarily removes a majority of the first extraction solvent from the mixture of the fluid in a manner similar to the removal process for lipid that occurs in the initial phase susbsystem. The second extraction solvent additionally removes a portion of any residual lipids remaining in the fluid. After the second extraction solvent has flowed through the HFC on the shell side of the hollow fibers in the intermediate subsystem, the second extraction solvent is deposited in an extraction solvent waste receptacle. After leaving the intermediate phase subsystem, the fluid contains a fraction of the original lipids, a fraction of the first extraction solvent, and a minimal amount of the second extraction solvent. Once the mixture of the fluid containing the first and second extraction solvents has passed through the intermediate phase subsystem, the mixture is transferred to the final phase subsystem.

The final phase subsystem may be composed of a once-through system, a recirculating system, or another system for removing solvents. The once-through system and the recirculating system are similar in design but have different configurations. Generally in either system, the fluid passes through at least one HFC where it is exposed to a gas to remove at least a portion of any remaining solvents. The volatile solvent in the fluid evaporates into the gas stream. In another embodiment, the gas may be replaced with mineral oil. Removal of these solvents is accomplished by passing the mixture through the hollow fibers of the HFC while the gas is passed through the HFC on the shell side of the hollow fibers as many times as necessary to remove the solvents. The gas removes the solvents and is passed through a gas filter loop, which may be composed of a carbon bed, a pump, at least one pressure regulator, and at least one filter, for removing the solvents from the gas. In other embodiments, the carbon bed may be replaced by one or more filters, condensers or cold traps, or catalytic combusters to remove the solvent vapors from the gas before it is recycled through the HFC. At this point, the fluid can be safely returned to the donor, stored, or transferred to another patient to be administered for therapeutic purposes. If the recirculating final phase subsystem is used, the fluid must be sent through the system multiple times before the solvent level is reduced to a safe level in the fluid. A sensor may be used to determine when sufficient amounts of solvents have been removed from the fluid.

In an alternative embodiment, any one of the subsystems described above, or any combination of these subsystems, may be replaced by a subsystem having at least two HFCs in parallel. This parallel subsystem allows a fluid, or a mixture of a fluid and an extraction solvent, to flow through the hollow fibers of at least one first HFC while a second HFC is not used. This parallel subsystem includes sensors for detecting lipids and is coupled to a control system that redirects the flow from the first HFC to the second HFC when it detects the presence of lipids above a predetermined threshold. Once the flow has been changed, the first HFC can be washed, replaced, receive a reverse flow, or be reoriented. This parallel subsystem enables the delipidation system to have the capacity to run the fluid or mixture through an operable HFC at all times. In yet another alternative embodiment, a single HFC may be used to accomplish all three steps of this delipidation process.

An advantage of this invention is that fluids containing lipids and lipid containing organisms can be delipidated in a time efficient manner because the fluid need only travel once through the system.

Another advantage of this invention is that fluid can be processed in a continuous manner and returned to a patient without requiring withdrawal of an unacceptable amount of blood from the patient.

Yet another advantage of this invention is that the system uses HFCs to complete all aspects of the process, thereby minimizing the number of moving parts within the system and the likelihood of failure resulting from moving parts.

Still another advantage of this invention is that by removing lipids from lipid-containing organisms, the infectivity of those organisms is reduced as well.

These and other features and advantages of the present invention will become apparent after review of the following drawings and detailed description of the disclosed embodiments.

BRIEF DESCRIPTION OF THE DRAWINGS

The accompanying drawings, which are incorporated in and form a part of the specification, illustrate preferred embodiments of the present invention and, together with the description, disclose the principles of the invention.

FIG. 3 is a schematic diagram of an embodiment of this invention showing a recirculating final phase subsystem.

DETAILED DESCRIPTION OF THE INVENTION

Figure 1:
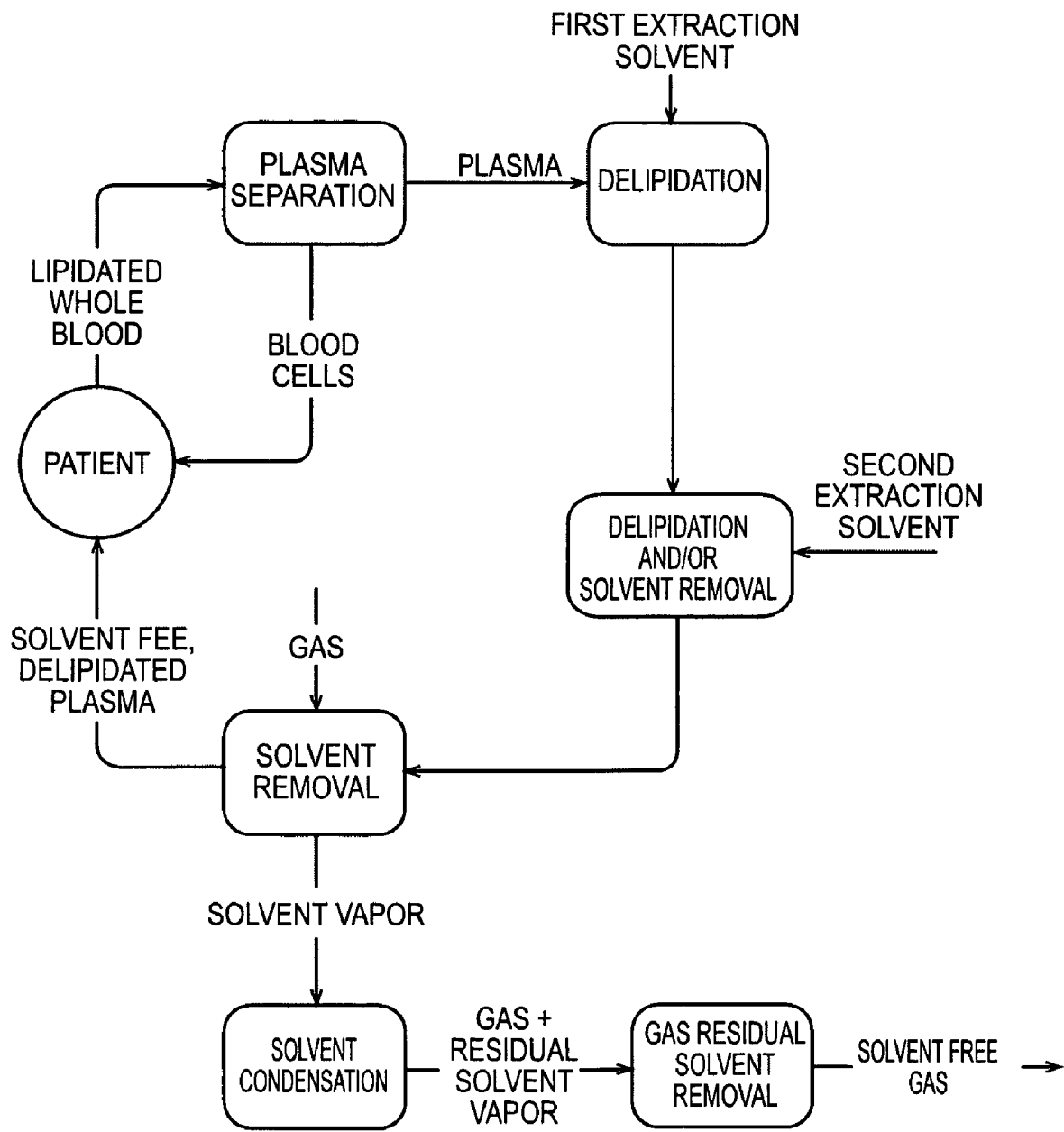
FIG. 1 is a block diagram of an embodiment of this invention.

This invention relates to systems, apparatus and methods useful for delipidation of fluids in animals, including humans. In a preferred embodiment, the fluid is plasma; however, the fluid can be composed of other materials, as described below. This system and apparatus can treat arteriosclerosis and atherosclerotic vascular diseases, and remove lipid from lipid-containing organisms or infectious agents circulating within the blood of animals and humans, thereby rendering these organisms less infective.

I. Definitions and Solvents

A. Definitions

The term "fluid" is defined as fluids from animals or humans that contain lipids, fluids from culturing tissues and cells that contain lipids, fluids mixed with lipid-containing cells, and fluids mixed with lipid-containing organisms. For purposes of this invention, delipidation of fluids include delipidation of cells and organisms in a fluid. Fluids include, but are not limited to: biological fluids, such as, blood, plasma, serum, lymphatic fluid, cerebrospinal fluid, peritoneal fluid, pleural fluid, pericardial fluid; various fluids of the reproductive system including, but not limited to, semen, ejaculatory fluids, follicular fluid and amniotic fluid; cell culture reagents such as normal sera, fetal calf serum or serum derived from any animal or human; and immunological reagents, such as various preparations of antibodies and cytokines, from culturing tissues and cells, fluids mixed with lipid-containing cells, and fluids containing a lipid-containing organisms, such as a saline solution containing lipid-containing organisms.

The term "hollow fiber contactor" (HFC) is defined as being any conventional HFC or other HFC. Typically, HFCs have an outer body, referred to as a shell and forming a chamber, for containing a plurality of hollow fibers positioned generally parallel to a longitudinal axis of the shell. The hollow fibers are generally cylindrical tubes having small diameters formed by a permeable membrane having pores that allow certain materials to pass through the membrane. The HFC is designed to allow a first material to pass through the lumens of the hollow fibers and a second material to pass through the HFC on the shell side of the hollow fibers. The first material may pass from the lumens of the hollow fibers, through the pores of the hollow fibers and into the second material on the shell side of the hollow fibers, or vice versa. The ability for the materials to pass through the pores of the hollow fibers is predicated on numerous factors, such as pore size, pressure, flow rate, solubility, and others.

The term "lipid" is defined as any one or more of a group of fats or fat-like substances occurring in humans or animals. The fats or fat-like substances are characterized by their insolubility in water and solubility in organic solvents. The term "lipid" is known to those of ordinary skill in the art and includes, but is not limited to, complex lipid, simple lipid, triglycerides, fatty acids, glycerophospholipids (phospholipids), true fats such as esters of fatty acids, glycerol, cerebrosides, waxes, and sterols such as cholesterol and ergosterol.

The term "lipid" is also defined as including lipid-containing organisms or lipid-containing infectious agents. Lipid-containing infectious agents are defined as any organism or agent containing lipids. Such lipids may be found, for example, in a bacterial cell wall or viral envelope. Lipid-containing organisms include, but are not limited to, eukaroyotic and prokaryotic organisms, bacteria, viruses, protozoa, mold, fungi, and other lipid-containing parasites.

The term "infectious organism" means any lipid-containing infectious organism capable of causing infection. Some infectious organisms include bacteria, viruses, protozoa, parasites, fungi and mold. Some bacteria which may be treated with the method of this invention include, but are not limited to, the following: *Staphylococcus; Streptococcus*, including *S. pyogenes; Enterococci; Bacillus*, including *Bacillus anthracis*, and *Lactobacillus; Listeria; Corynebacterium diphtheriae; Gardnerella* including *G. vaginalis; Nocardia; Streptomyces; Thermoactinomyces vulgaris; Treponema; Camplyobacter; Pseudomonas* including *P. aeruginosa; Legionella; Neisseria* including *N. gonorrhoeae* and *N. meningitides; Flavobacterium* including *F. meningosepticum* and *F. odoratum; Brucella; Bordetella* including *B. pertussis* and *B. bronchiseptica; Escherichia* including *E. coli; Klebsiella; Enterobacter; Serratia* including *S. marcescens* and *S. liquefaciens; Edwardsiella; Proteus* including *P. mirabilis* and *P. vulgaris; Streptobacillus; Rickettsiaceae* including *R. rickettsii; Chlamydia* including *C. psittaci* and *C. trachomatis; Mycobacterium* including *M. tuberculosis, M. intracellulare, M. fortuitum, M. laprae, M. avium, M. bovis, M. africanum, M. kansasii, M. intracellulare*, and *M. lepraemurium*; and *Nocardia*, and any other bacteria containing lipid in their membranes.

Viral infectious organisms which may be inactivated by the above system include, but are not limited to, the lipid-containing viruses of the following genuses: *Alphavirus* (alphaviruses), *Rubivurus* (rubella virus), *Flavivirus* (Flaviviruses), *Pestivirus* (mucosal disease viruses), (unnamed, hepatitis C virus), *Coronavirus*, (Coronaviruses), *Torovirus*, (toroviruses), *Arteivirus*, (arteriviruses), *Paramyxovirus*, (Paramyxoviruses), *Rubulavirus* (rubulavriuses), *Morbillivirus* (morbillivuruses), *Pneumovirinae* (the pneumoviruses), *Pneumovirus* (pneumoviruses), *Vesiculovirus* (vesiculoviruses), *Lyssavirus* (lyssaviruses), *Ephemerovirus* (ephemeroviruses), *Cytorhabdovirus* (plant rhabdovirus group A), *Nucleorhabdovirus* (plant rhabdovirus group B), *Filovirus* (filoviruses), *Influenzavirus A, B* (influenza A and B viruses), *Influenza virus C* (influenza C virus), (unnamed, Thogoto-like viruses), *Bunyavirus* (bunyaviruses), *Phlebovirus* (phleboviruses), *Nairovirus* (nairoviruses), *Hantavirus* (hantaviruses), *Tospovirus* (tospoviruses), *Arenavirus* (arenaviruses), unnamed mammalian type B retroviruses, unnamed, mammalian and reptilian type C retroviruses, unnamed type D retroviruses, *Lentivirus* (lentiviruses), *Spumavirus* (spumaviruses), *Orthohepadnavirus* (hepadnaviruses of mammals), *Avihepadnavirus* (hepadnaviruses of birds), *Simplexvirus* (simplexviruses), *Varicellovirus* (varicelloviruses), *Betaherpesvirinae* (the cytomegaloviruses), *Cytomegalovirus* (cytomegaloviruses), *Muromegalovirus* (murine cytomegaloviruses), *Roseolovirus* (human herpes virus 6), *Gammaherpesvirinae* (the lymphocyte-associated herpes viruses), *Lymphocryptovirus* (Epstein-Bar-like viruses), *Rhadinovirus* (saimiri-ateles-like herpes viruses), *Orthopoxvirus* (orthopoxviruses), *Parapoxvirus* (parapoxviruses), *Avipoxvirus* (fowlpox viruses), *Capripoxvirus* (sheeppoxlike viruses), *Leporipoxvirus* (myxomaviruses), *Suipoxvirus* (swine-pox viruses), *Molluscipoxvirus* (molluscum contagiosum viruses), *Yatapoxvirus* (yabapox and tanapox viruses), Unnamed, African swine fever-like viruses, *Iridovirus* (small iridescent insect viruses), *Ranavirus* (front iridoviruses), *Lymphocystivirus* (lymphocystis viruses of fish), *Togaviridae, Flaviviridae, Coronaviridae, Enabdoviridae, Filoviridae, Paramyxoviridae, Orthomyxoviridae, Bunyaviridae, Arenaviridae, Retroviridae, Hepadnaviridae, Herpesviridae, Poxyiridae*, and any other lipid-containing virus.

These viruses include the following human and animal pathogens: Ross River virus, fever virus, dengue viruses, Murray Valley encephalitis virus, tick-borne encephalitis viruses (including European and far eastern tick-borne encephalitis viruses, human coronaviruses 229-E and OC43 and others (causing the common cold, upper respiratory tract infection, probably pneumonia and possibly gastroenteritis), human parainfluenza viruses 1 and 3, mumps virus, human parainfluenza viruses 2, 4a and 4b, measles virus, human respiratory syncytial virus, rabies virus, Marburg virus, Ebola virus, influenza A viruses and influenza B viruses, *Arenaviruss*: lymphocytic choriomeningitis (LCM) virus; Lassa virus, human immunodeficiency viruses 1 and 2, or any other immunodeficiency virus, hepatitis A virus, hepatitis B virus, hepatitis C virus, Subfamily: human herpes viruses 1 and 2, herpes virus B, Epstein-Barr virus), (smallpox) virus, cowpox virus, molluscum contagiosum virus.

All protozoa containing lipid, especially in their plasma membranes, are included within the scope of the present invention. Protozoa that may be inactivated by the system and apparatus of the present invention include, but are not limited to, the following lipid-containing protozoa: *Trypanosoma brucei, Trypanosoma gambiense, Trypanosoma cruzi, Leishmania donovani, Leishmania vianni, Leishmania tropica, Giardia lamblia, Giardia intestinalis, Trichomonas vaginalis, Entamoeba histolytica, Entamoeba coli, Entamoeba hartmanni, Naegleria* species, *Acanthamoeba* species, *Plasmodium falciparum, Plasmodium vivax, Plasmodium malariae, Plasmodium ovale, Toxoplasma gondii, Cryptosporidium parvum, Cryptosporidium muris, Isospora belli, Cyclospora cayetansis, Balantidium* species, *Babesia bovis, Babesia, microti, Babesia divergens, Encephalitozoon intestinalis, Pleistophora* species, *Nosema ocularum, Vittaforma corneae, Septata intestinalis, Enterocytozoon, Dientamoeba fragilis, Blastocystis* species, *Sarcocystis* species, *Pneumocystis carinii, Microsporidium africanum, Microsporidium ceylonensis, Eimeria acervulina, Eimeria maxima, Eimeria tenella* and *Neospora caninum* and any other lipid-containing protozoa. It is to be understood that the present invention is not limited to the protozoa provided in the list above.

A preferred protozoa treated with the method of the present invention is Coccidia, which includes *Isospora* species, *Cryptosporidium* species, *Cyclospora* species, *Toxoplasma* species, *Sarcocystis* species, *Neospora* species, and *Eimeria* species. These coccidian parasites cause intestinal disease, lymphadenopathy, encephalitis, myocarditis, and pneumonitis.

The terms "protozoal infection" or "infectious disease" mean diseases caused by protozoal infectious organisms. The diseases include, but are not limited to, African sleeping sickness, Chagas' disease, Leishmaniasis, Giardiasis, Trichomoniasis, amebiasis, primary amebic encephalitis, granulomatous amebic encephalitis, malaria, Toxoplasmosis, Cryptosporidiosis, Isosporiasis, Cyclosporiasis, Balantidiasis, Babesiosis, microsporidiosis, Dientamoeba fragilis infection, Blastocystis hominis infection, Sarcosporidiosis, pneumonia, and coccidiosis. A preferred protozoal infection treated with the method of the present invention is Coccidiosis, which is caused by *Isospora* species, *Cryptosporidium* species, *Cyclospora* species, *Toxoplasma* species, *Sarcocystis* species, *Neospora* species, and *Eimeria* species. These coccidian parasites cause human intestinal disease, lymphadenopathy, encephalitis, myocarditis, and pneumonitis. These coccidian parasites also cause disease in animals, including cattle, dogs, cats, and birds. Avians, and chickens, turkeys and quail in particular, are affected by Coccidiosis, especially by *Eimeria* species such as *E. acervulina, E. maxima, E. necatrix, E. bruneti, E. mitis, E. praecox* and *E. tenella*.

The term "continuous" refers to the process of delipidating a fluid, such as plasma, while the animal or human remains connected to an apparatus for delipidating the fluid. Additionally, "continuous" refers to the internal processes of the lipid removal system, wherein the fluid continually flows within the lipid removal system from subsystem to subsystem.

The term "batch" refers to the process of delipidating a fluid, such as plasma, without returning or passing the delipidated fluid directly to the animal or human during the delipidation process. Rather, the delipidated fluid is stored. Additionally, "batch" refers to the internal process of the lipid removal machine, wherein the fluid does not continually flow within the lipid removal system from subsystem to subsystem.

The term "delipidation" refers to the process of removing at least a portion of a total concentration of lipids from a fluid or from a lipid-containing organism.

The term "first extraction solvent" is defined as one or more solvents used in the initial stage subsystem for extracting lipids from a fluid containing lipids or from lipid-containing organisms. The first extraction solvent enters the fluid and remains in the fluid until removed by other subsystems. Suitable extraction solvents include solvents that extract or dissolve lipids, including, but not limited to, alcohols, phenols, hydrocarbons, amines, ethers, esters, halohydrocarbons, halocarbons, and combinations thereof. Preferred first extraction solvents are combinations of alcohols and ethers, which include, but are not limited to, n-butanol, di-isopropyl ether or isopropyl ether, which are both referred to as (DiPE), diethyl ether (DEE), sevoflourane, perfluorocyclohexanes, trifluoroethane, isoflurane, cyclofuorohexanol and combinations thereof.

The term "second extraction solvent" is defined as one or more solvents that facilitate removal of at least a portion of the first extraction solvent. Suitable second extraction solvents include any solvent that facilitates removal of the first extraction solvent mixed with or exposed to the fluid containing lipids or lipid-containing organisms, or both. Second extraction solvents include any solvent that facilitates removal of the first extraction solvent including, but not limited to, ethers, alcohols, phenols, hydrocarbons, amines, esters, halohydrocarbons, halocarbons, and combinations thereof. Preferred second extraction solvents include an ether, such as diethyl ether, which facilitates removal of lower order alcohols, such as n-butanol, from the fluid.

The term "patient" refers to animals and humans, which may be either a fluid source or a recipient of delipidated fluid or delipidated organisms.

B. Solvents

Numerous organic solvents may be used in the method of this invention for removal of lipid from fluids and from lipid-containing organisms, especially infectious organisms, provided that the solvents or combinations thereof are effective in solubilizing lipids. Suitable solvents comprise mixtures of hydrocarbons, ethers, alcohols, phenols, esters, halohydrocarbons, halocarbons and amines. Other solvents which may be used with this invention include amines and mixtures of amines. Preferred solvents are combinations of alcohols and ethers. Another preferred solvent comprises an ether or combinations of ethers. It is preferred that the solvent or combination of solvents has a relatively low boiling point to facilitate removal of the solvent via a combination of vacuum and possibly heat applications.

Examples of suitable amines for use in removal of lipids from lipid-containing organisms are those which are substantially water immiscible. Typical amines are aliphatic amines having a carbon chain of at least 6 carbon atoms. A non-limiting example of such an amine is $C_6H_{13}NH_2$. Another suitable amine is perfluorotributyl amine.

The alcohols which are preferred for use in this invention, when used alone, include those alcohols that are not appreciably miscible with plasma or other fluids. Such alcohols include, but are not limited to, straight chain and branched chain alcohols, including pentanols, hexanols, heptanols, octanols, and alcohols containing higher numbers of carbons. Halogenated alcohols may be employed, including, but not limited to, heptafluoro-butanol.

When alcohols are used in combination with another solvent, for example, an ether, a hydrocarbon, an amine, or a combination thereof, $C_1$–$C_8$ containing alcohols may be used. Preferred alcohols for use in combination with another solvent include $C_4$–$C_8$ containing alcohols. Accordingly, preferred alcohols are butanols, pentanols, hexanols, such as 1-hexanol, heptanols, octanols, and ethanols, and iso forms thereof. Particularly preferred are the butanols (1-butanol and 2-butanol). As stated above, the most preferred alcohol is the $C_4$ alcohol, butanol. The specific choice of alcohol will depend on the second solvent employed. In a preferred embodiment, lower alcohols are combined with lower ethers.

Ethers, used alone, or in combination with other solvents, preferably alcohols, are another preferred solvent for use in the method of the present invention. Particularly preferred ethers are the $C_4$–$C_8$ containing-ethers, including but not limited to, diethyl ether, and propyl ethers, including, but not limited to, di-isopropyl ether. Asymmetrical ethers and halogenated ethers may also be employed. Also useful in the present invention are combinations of ethers, such as di-isopropyl ether and diethyl ether. When ethers and alcohols are used in combination as a first solvent for contacting the fluid containing lipids or lipid-containing organisms, or both, any combination of alcohol and ether may be used provided the combination is effective to partially or completely remove lipids from the fluid or the lipid-containing organism.

In one embodiment, lipids are removed from the viral envelope or bacterial cell wall of the infectious organism, which reduces the infectivity of the virus or bacteria. When alcohols and ether are combined as a first extraction solvent for removing lipids from a fluid containing lipids or lipid-containing organisms, or both, preferred ratios of alcohol to ether in this solvent are about 0.01%–60% alcohol to about 40%–99.99% of ether, with a preferred ratio of about 10%–50% of alcohol with about 50%–90% of ether, with a most preferred ratio of about 20%–45% alcohol and about 55%–80% ether. An especially preferred combination of alcohol and ether is the combination of butanol and di-isopropyl ether. Another especially preferred combination of alcohol and ether is the combination of butanol with diethyl ether.

When butanol and di-isopropyl ether are combined as a first extraction solvent for removing lipids from a fluid containing lipids or from lipid-containing organisms, or both, contained in a fluid, preferred ratios of butanol to di-isopropyl ether in this solvent are about 0.01%–60% butanol to about 40%–99.99% of di-isopropyl ether, with a preferred ratio of about 10%–50% of butanol with about 50%–90% of di-isopropyl ether, with a most preferred ratio of about 20%–45% butanol and about 55%–80% di-isopropyl ether. The most preferred ratio of butanol and di-isopropyl ether is about 40% butanol and about 60% di-isopropyl ether.

When butanol is used in combination with diethyl ether in a first extraction solvent, preferred ratios of butanol to diethyl ether in this combination are about 0.01%–60% butanol to about 40%–99.99% diethyl ether, with a preferred ratio of about 10%–50% butanol with about 50%–90% diethyl ether, with a most preferred ratio of about 20%–45% butanol and about 55%–80% diethyl ether. The most preferred ratio of butanol and diethyl ether in a first solvent is about 40% butanol and about 60% diethyl ether.

Hydrocarbons in their liquid form dissolve compounds of low polarity such as the lipids in fluids and lipids found in membranes of organisms. Hydrocarbons which are liquid at about 37° C. are effective in disrupting a lipid membrane of an infectious organism. Accordingly, hydrocarbons comprise any substantially water immiscible hydrocarbon which is liquid at about 37° C. Suitable hydrocarbons include, but are not limited to, the following: $C_5$ to $C_{20}$ aliphatic hydrocarbons such as petroleum ether, hexane, heptane, and octane; haloaliphatic hydrocarbons such as chloroform, trifluoroethane, 1,1,2-trichloro-1,2,2-trifluoroethane, 1,1,1-trichloroethane, trichloroethylene, tetrachloroethylene dichloromethane and carbon tetrachloride; thioaliphatic hydrocarbons; perfluorocarbons, such as perfluorocyclohexane, perfluorohexane, perfluoromethylcyclohexane, and perfluorodimethylcyclohexane; fluroethers such as sevoflurane; each of which may be linear, branched or cyclic, saturated or unsaturated; aromatic hydrocarbons such as benzene; alkylarenes such as toluene, haloarenes, haloalkylarenes and thioarenes. Other suitable solvents may also include: saturated or unsaturated heterocyclic compounds such as water insoluble derivatives of pyridine and aliphatic, thio or halo derivatives thereof; and perfluorooctyl bromide. Another suitable solvent is perfluorodecalin.

II. Overview

For purposes of explanation, the removal of lipids from plasma, termed delipidation, is discussed in detail. However, this is not meant to limit the application of the invention solely to delipidation of plasma. Rather, the same principles and process apply to other fluids and to removal of lipids from lipid-containing organisms. The delipidation system 10 of this invention receives fluid from a patient, or other source, removes lipids contained within the fluid, and returns the delipidated fluid to the patient, or other source. The delipidation system of this invention may be used as a continuous system, by returning fluid to a patient immediately after lipids have been removed, or as a batch system by removing lipids from the fluid without immediately returning the fluids to the patient.

In one embodiment of this invention, as shown in FIG. 1, the invention may be used to delipidate plasma. For instance, whole blood is drawn from a patient using conventional procedures and subjected to a conventional plasma separation process. Such cellular separation systems include, but are not limited to, apheresis and plasmapheresis systems, such as SPECTRA and TRIMA manufactured by Cobe BCT, Gambro BCT, Lakewood, Colo.; AUTOPHERESIS-C manufactured by Baxter Healthcare Corporation, Deerfield, Ill.; or AS104 manufactured by Fresenius, Berlin, Germany. In another embodiment, blood is combined with an anticoagulant, such as sodium citrate, and centrifuged at forces approximately equal to 2,000 times gravity. The red blood cells are then aspirated from the plasma. This plasma separation process returns the blood cells to the patient and collects the plasma. The plasma, or lipid-containing organisms therein, are then subjected to the lipid removal process of this invention, which is described in detail below.

In general, the delipidation method includes multiple phases including, but not limited to, an initial phase, an intermediate phase, and a final phase. The initial phase removes lipids from a fluid, for example plasma, or from at least one lipid-containing organism, using a first extraction solvent. The intermediate phase completes the delipidation process and removes at least a portion of the first extraction solvent, as well as residual lipids, from the fluid using a second extraction solvent. The final phase removes the remainder of the first extraction solvent and the majority of the second extraction solvent from the fluid using an inert gas, such as air, or mineral oil, so that the delipidated fluid can be administered to a patient. The delipidated plasma is then in a condition to be returned to the patient or stored for administration to another patient for therapeutic applications.

III. The Delipidation System

Figure 2:
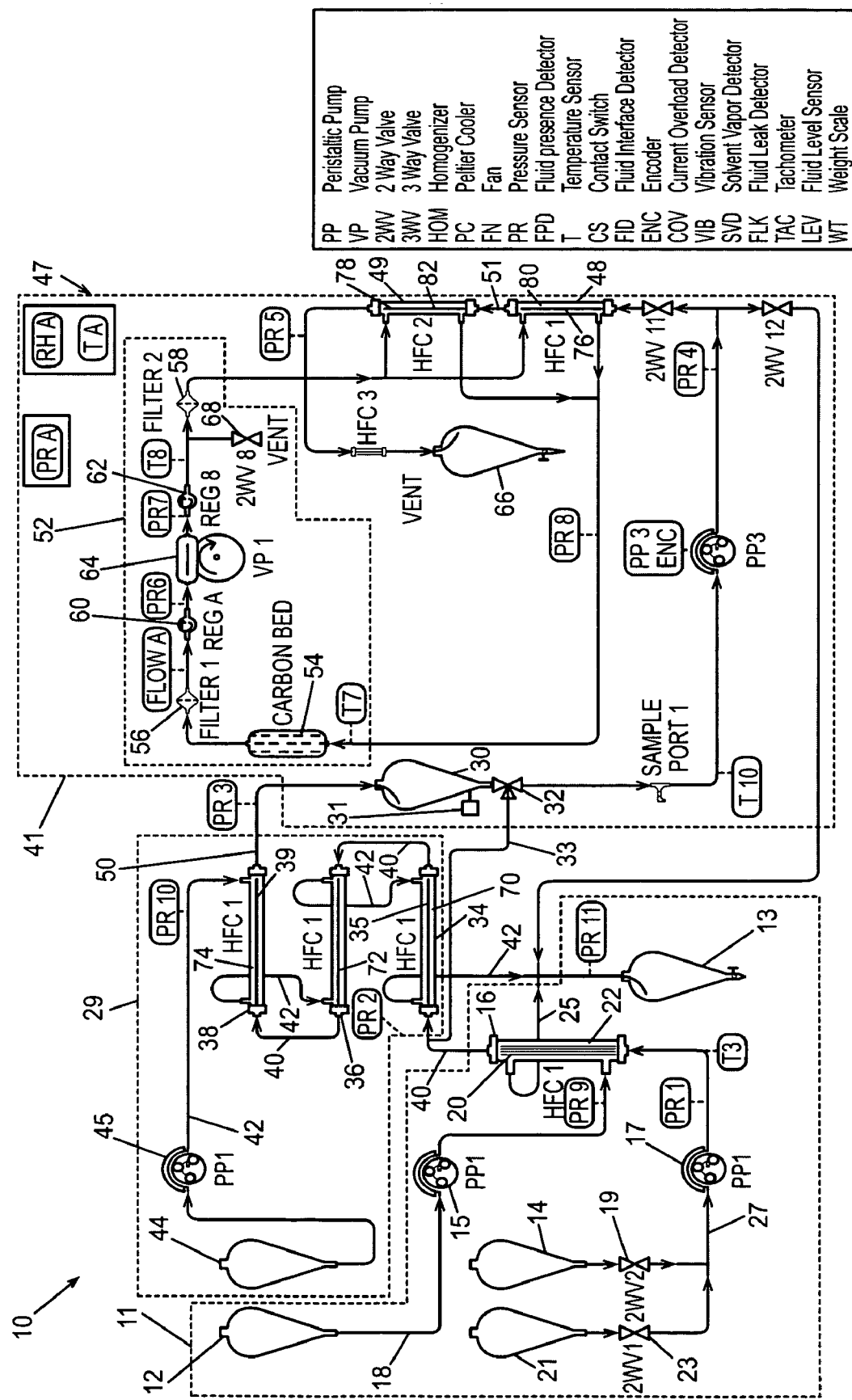
FIG. 2 is a schematic diagram of an embodiment of this invention showing an initial phase subsystem, an intermediate phase subsystem, and a final phase subsystem, wherein the final phase subsystem is a once-through final phase subsystem.
Figure 1:
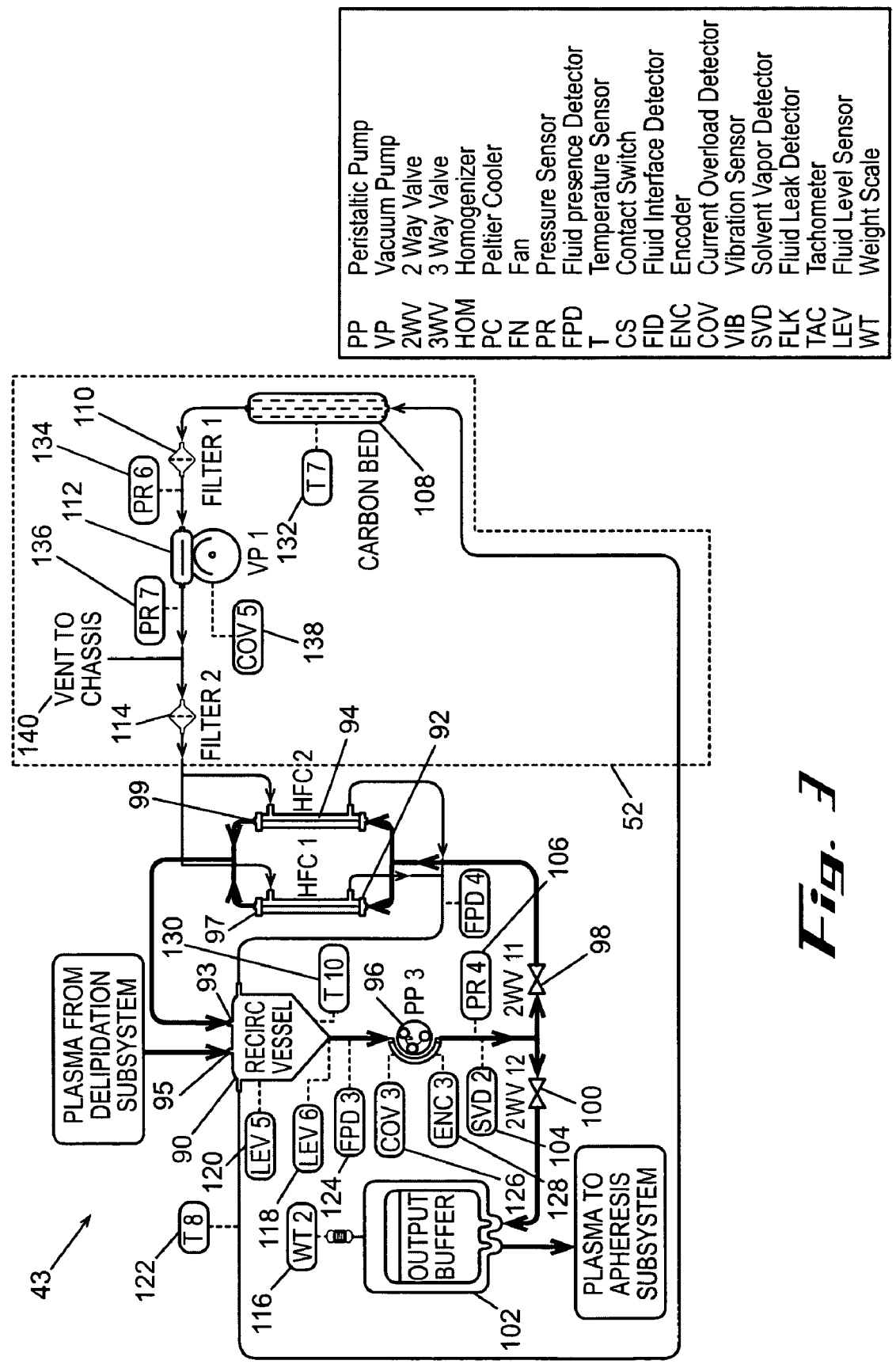

The delipidation system 10 is composed of at least three phases for delipidating a fluid containing lipids or lipid-containing organisms, or both, which include an initial phase, an intermediate phase, and a final phase. As is illustrated in FIG. 2, the initial phase may be carried out using an initial phase subsystem 11 composed of a first extraction solvent source 12, an extraction solvent waste receptacle 13, a fluid source 14, and at least one hollow fiber contactor (HFC) 16. The intermediate phase may be carried out using intermediate phase subsystem 29, which may include at least one HFC, and in one embodiment, may include three HFCs 34, 36 and 38, for completing the delipidation process and removing at least a portion of the first extraction solvent. The final phase may be carried out using final phase subsystem 47, which may be composed of either a once-through final phase subsystem 41 or a recirculating final phase subsystem 43 shown in FIG. 3, both of which are composed of at least one HFC.

The number of HFCs used in each subsystem may be dictated by the amount of lipids desired to be removed. The number and size of the HFCs are a function of the flow rate of fluids or gases within the hollow fibers and in the chamber formed by the shell of the HFC and the outside surfaces of the hollow fibers, the porosity of the hollow fibers, and the amount of surface area of the hollow fiber. Adjusting one of these factors requires the other factors be changed in order to yield the same output at the same rate. Additionally, patients having a higher initial starting level of lipids may require greater surface area of hollow fibers to be used to obtain therapeutic effects.

A. Initial Phase Subsystem

Figure 4:
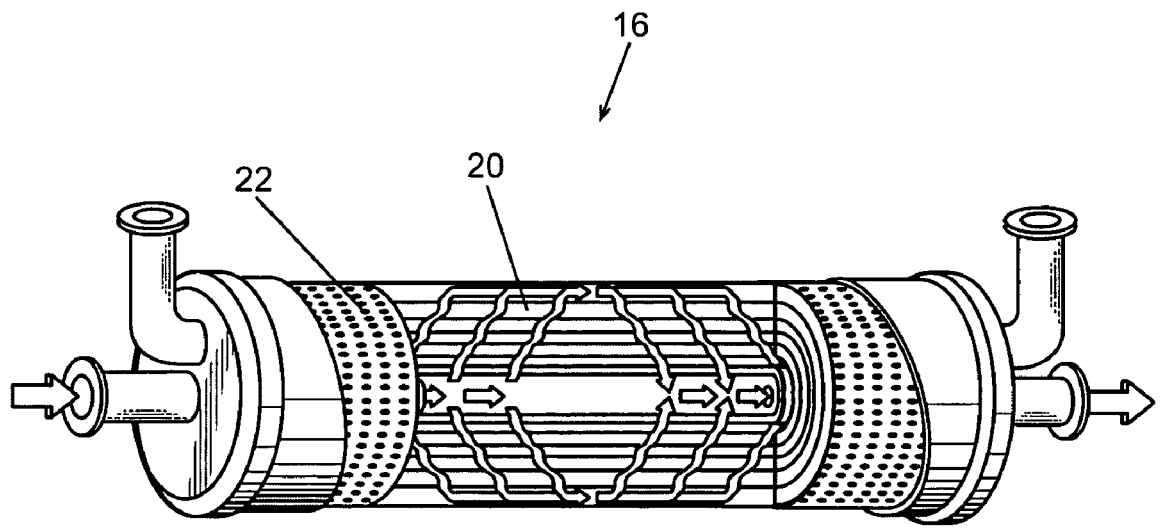
FIG. 4 is a perspective view of a HFC with a partial cut away section.
Figure 5:
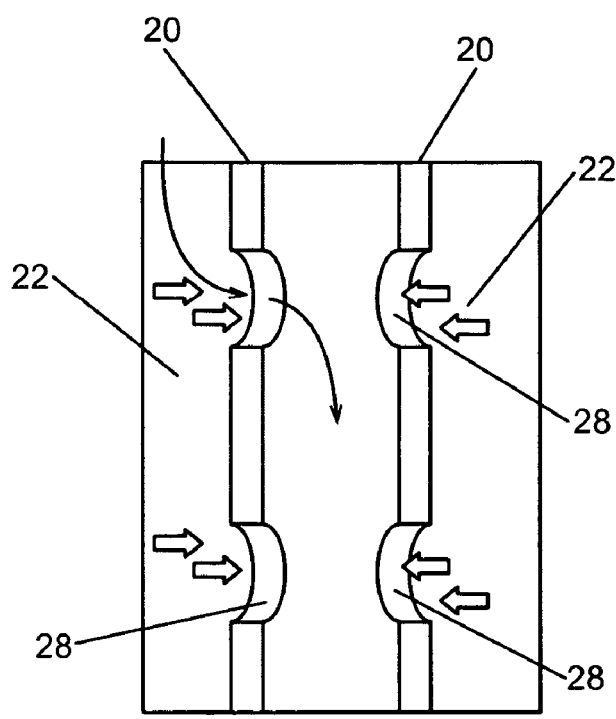
FIG. 5 is cross-sectional view of a portion of a hollow fiber of a HFC, according to another aspect of the present invention.

Initial phase subsystem 11 is used to at least partially delipidate a fluid. In one embodiment, a substantial amount of the lipid may be removed from a fluid within initial phase subsystem 11 using at least one HFC 16 and a first extraction solvent. Initial phase subsystem 11 may include two or more HFCs 16 coupled in series or parallel, or any combination thereof, such as the configuration shown as final phase subsystem 43 and 41 in FIGS. 2 and 3. As shown in FIG. 2 and in more detail in FIGS. 4 and 5, HFC 16 has a generally cylindrical body that contains a plurality of hollow fibers 20, which typically number between about 3,000 and about 5,000, and a chamber 22 formed by the inside surface of the cylindrical exterior wall of HFC 16, referred to as the shell side of the membranes. Each hollow fiber 20 is a cylindrical tube formed from a membrane having a small diameter, such as between about 0.2 millimeters and about 1.0 millimeters, and pores 28 sized to allow gases and liquids to pass through hollow fiber 20. Hollow fibers 20 are positioned in a HFC so that their longitudinal axes are generally parallel to the longitudinal axis of the HFC. Pores 28 need only be large enough to allow the first and second extraction solvents to diffuse through pores 28 into the plasma and for the lipids to diffuse through pores 28 and into the solvents or attach to the inside surfaces of hollow fibers 20 or pores 28. Pores 28 may have a diameter within the range of between about 5 kilodaltons and about 500 kilodaltons or between about 3 nanometers and about 300 nanometers. Varying the size of pores 28 can allow either more or less materials to pass through pores 28.

While not being bound by the following statements, the following discussion is a possible explanation of the operation of the system at the pores 28 of the hollow fibers 20. The hollow fibers 20 may be formed of either hydrophobic or hydrophilic materials. If hollow fibers 20 formed from a hydrophobic material are used, the solvent fills pores 28, and an interface forms between the solvent in pores 28 and the fluid that remains in the lumens. The solvent diffuses across the interface into the fluid, but there is minimal, if any, mixing of the fluid and the solvent. Thus, there exists very little possibility of an emulsion forming. The lipids that may have been solubilized by the action of the solvents diffuse into the solvent in the pores 28 at the interface. The lipids continue to diffuse through pores 28 until the lipids are swept away by the solvent flowing through HFC 16 on the shell side of the lumens. If a hydrophilic material is used to form hollow fibers 20, pores 28 fill with fluid, and the solvent does not fill pores 28. The lipids then diffuse through pores 28.

The preferred material is a hydrophobic material because the highest transport rate is achieved when pores 28 are filled with the material having the highest solubility for the material desired to be passed through pores 28. In this case, lipids are more soluble in the solvents described above than in the fluid. Thus, a hydrophobic material is preferred.

The flow rate of the fluid and first extraction solvent dictates the required amount of permeable surface area on hollow fibers 20. For instance, the slower the flow rate, the smaller the surface area required, and conversely, the faster the flow rate, the larger the surface area required. This is dictated by a mass transport formula. The formula below illustrates the situation for a soluble gas:

$$Q_1(C_{in} - C_{out}) = K_1 A_m \Delta C_{lm} = K_l A_m \frac{\left(C_{in} - \frac{P_{out}}{H}\right) - \left(C_{out} - \frac{P_{in}}{H}\right)}{\ln \frac{C_{in} - \frac{P_{out}}{H}}{C_{out} - \frac{P_{out}}{H}}}$$

where $C_{out}$ represents the liquid phase concentration (output), $C_{in}$ represent the liquid phase concentration (input), $K_1$ represents the overall mass transport coefficient, $A_m$ represents the total membrane contact area, $Q_1$ represents the liquid flow rate, H represents the Henry's Law coefficient and P represents the gas phase partial pressure. If $P_{in}$ and $P_{out}$ are small in magnitude and/or H is large, the terms P and H are negligible. In this case, the first equation simplifies to:

$$C_{out} = C_{in} \ln\left(-\frac{K_l A_m}{Q_1}\right).$$

Examples of commercially available HFCs are the CELGARD mini model no. G471, G476, G478, or G495 available from CelGard, Charlotte, N.C., and the Spectrum MINIKROS model no. M21S-600-01N, available from Spectrum Laboratories, Inc., Rancho Dominguez, Calif.

The first extraction solvent source 12 may be any device or system capable of the supplying a first extraction solvent to system 10. First extraction solvent source 12 is coupled to chamber 22 of HFC 16 using conduit 18, which can be formed from pipe, tubing, or other such devices. The first extraction solvent may be feed to chamber 22 via gravity, pump 15, or other such means. Pump 15 is coupled to conduit 18 between first extraction solvent source 12 and HFC 16 for pumping the first extraction solvent from first extraction source 12 to HFC 16. In one embodiment, pump 15 is a peristaltic pump, such as MASTERFLEX L/S model number 07523-40 available from Cole Parmer Instrument Company, Vernon Hills, Ill., or other pumps not having vanes that contact the fluid being pumped.

In one embodiment, initial phase subsystem 11 includes an extraction solvent waste receptacle 13 that is coupled to HFC 16 using conduit 25 for containing the first extraction solvent after it has passed from first extraction solvent source 12 through HFC 16. First extraction solvent source 12 and extraction solvent waste receptacle 13 may be composed of a tank, a flask, or other devices known to those skilled in the art for containing solvents.

Fluid source 14 is coupled to HFC 16 using conduit 27. Fluid source 14 may be composed of a tank, a flask, a plasmapheresis bag, and other devices known to those skilled in the art for containing a fluid. In one embodiment, a pump 17 is coupled to conduit 27 between fluid source 14 and HFC 16 for transferring fluid from fluid source 14 to HFC 16. Pump 17 can be a peristaltic pump, such as MASTERFLEX L/S model number 07523-40 available from Cole Parmer Instrument Company, Vernon Hills, Ill., or other pumps not having vanes that contact the fluid being pumped. A valve 19 can be located between fluid source 14 and HFC 16, and, more specifically, between fluid source 14 and pump 17 for controlling the release of fluids from fluid source 14. Valve 19 can be composed of, but is not limited to, pinch, globe, ball, gate, or other conventional valves.

A saline fluid source 21 is coupled to HFC 16 using conduit 27 for containing a saline fluid and may be composed of a tank, sealed bag, flask or other similar device for containing fluids. Release of the saline fluid can be controlled using a valve 23 that may be similar or identical to valve 19.

B. Intermediate Phase Subsystem

System 10 further includes an intermediate phase subsystem 29 for completing the delipidation process and for removing a significant portion of the first extraction solvent from the mixture of fluid and first extraction solvent. This is accomplished by using at least one HFC to introduce a second extraction solvent to the mixture of the fluid and the first extraction solvent. In embodiments having two or more HFCs, the HFCs may be coupled together in series or in parallel, as shown in final phase subsystems 43 and 47 in FIGS. 2 and 3. In one embodiment, intermediate phase subsystem 29 includes three HFCs 34, 36, and 38, which each have generally the same integral components as HFC 16 and are coupled together in series. Three HFCs are used to obtain the proper amount of membrane surface area using commonly available conventional HFCs. The amount of surface area needed is determined using the mass transport formula described above. In one embodiment, the total permeable membrane surface area contained within the HFCs is about 3.3 square meters and is designed to be used with a flow rate of fluid of about 20 milliliters per minute and to reduce n-butanol, which was introduced in initial phase subsystem 11, from a concentration of approximately 40,000 parts per million (ppm) to about 0 ppm when washed with DiPE flowing at 40 milliliter per minute. However, the amount of surface area may vary depending on the factors set forth above. The plurality of hollow fibers 35, 37 and 39 of HFCs 34, 36 and 38 are coupled together using conduit 40, which can be composed of flexible or rigid pipe, tubing or other devices. Similarly, chambers 70, 72, and 74 of HFCs 34, 36 and 38 are coupled together using conduit 42, which can be composed of flexible or rigid pipe, tubing or other devices. In addition, intermediate phase subsystem 29 includes a second extraction solvent source 44, which is coupled to chamber 22 of HFC 38 through conduit 42.

In one embodiment, a pump 45 is coupled to conduit 42 between second extraction solvent source 44 and HFC 38 for transferring the second extraction solvent from second extraction solvent source 44 to HFC 38. Pump 45 can include, but is not limited to, a peristaltic pump, such as MASTERFLEX L/S model number 07523-40 from Cole Parmer Instrument Company, Vernon Hills, Ill., or other pumps. Extraction solvent waste receptacle 13 is coupled to chamber 22 of HFC 34 through conduit 42 to receive waste second extraction solvent.

C. Final Phase Subsystem

System 10 also includes final phase subsystem 47 for removing the first and second extraction solvents from the fluid so that the fluid can be safely administered to the patient from which the fluid was taken, to another patient for therapeutic applications, placed in storage for later use, or for another purpose. Final phase subsystem can be composed of at least two embodiments. One embodiment is capable of removing substantially all residual solvent from a fluid after passing the fluid through the system only one time. This system is referred to as a once-through final phase subsystem 41 and is shown schematically in FIG. 2. Another embodiment requires that the fluid be recirculated through a system multiple times to reduce the amount of residual solvent in the fluid to a level that will allow the fluid to be administered to a patient without the patient experiencing undesirable effects. This system is referred to as a recirculating final phase subsystem 43 and is shown schematically in FIG. 3.

1. Once-Through Solvent Removal Subsystem

In the once-through embodiment, final phase subsystem 41 is composed of at least one HFC 48. In one embodiment, final phase subsystem 41 is composed of at least two HFCs 48 and 49, each having the same general internal configuration as the HFCs previously described. HFC 48 includes a plurality of hollow fibers 76 that are coupled to a pervaporation buffer source 30 through conduit 50. Conduit 50 can be composed of flexible or rigid pipe, tubing or other such devices known to those of ordinary skill in the art. The plurality of hollow fibers 76 of HFC 48 are coupled to the hollow fibers 78 of HFC 49 through conduit 51. Final phase subsystem 41 may also include a delipidated fluid receptacle 66 for collecting the delipidated fluid after it has passed through HFCs 48 and 49. Delipidated fluid receptacle 66 may be composed of a flexible, sterile bag, a tank or other such device. In one embodiment, delipidated fluid receptacle 66 can be coupled directly to a patient for administering the delipidated fluid to the patient. However, the delipidated fluid receptacle 66 is not required to be coupled to a patient.

Final phase subsystem 41 also includes pervaporation buffer source 30, which may be coupled to conduit 50 between HFC 38 and HFC 48. Pervaporation buffer source 30 allows final phase subsystem 41 to be turned on or off using a valve. Pervaporation buffer source 30 includes a sensor 31 for detecting levels of first extraction solvents or second extraction solvents, or both, within the fluid. In one embodiment, sensor 31 can be adapted to detect an extraction solvent composed of n-butanol. In another embodiment, three-way valve 32 is coupled to conduit 50 for diverting fluid that sensor 31 has shown as containing a second solvent above a particular threshold to intermediate phase subsystem 29 through conduit 33.

Once-through final phase subsystem 41 includes a gas filtering loop 52 for removing the first and second extraction solvents from a gas used in the subsystem 41. In one embodiment, gas filtering loop 52 can include, but is not limited to, a carbon bed 54, a first filter 56, a second filter 58, a first pressure regulator 60, a second pressure regulator 62 and a pump 64. These elements may be coupled together using a conduit, a coupling or other connection device. Suitable filters may have a lipophilic or hydrophilic membranes. First and second filters 56 and 58 maybe sterile filters for preventing contamination of the system if pump 64 is removed. Carbon bed 54 is coupled to HFCs 48 and 49 for receiving gases having first and second extraction solvents. Carbon bed 54 removes most of the first and second extraction solvents from the gases being passed through the chambers 22 of HFCs 48 and 49. The remainder of the first and second extraction solvents are removed using first and second filters 56 and 58. Gas filtering loop 52 includes pump 64 for circulating the gases through the gas filtering loop 52 and through HFCs 48 and 49. Pump 64 may include, but is not limited to, a vacuum pump. Gas filtering loop 52 includes a vent 68 adapted to release the gas from loop 52 if desired. In other embodiments, the concentration of solvents in the gas loop may be reduced by using one or more filters, a condenser, a cold trap, or a catalytic combustor, in place of, or in addition to, the carbon bed.

HFCs 48 and 49 have been tested and successfully reduce total concentrations of solvents, such as di-isopropyl ether and di-ethyl ether, in water and plasmas, such as human and bovine plasma, using different HFCs, pressures, and flow rates, as shown in Table 1 below. Table 2 below shows the reduction in concentrations of DiPE in water, bovine plasma and human plasma as a function of time. HFCs 48 and 49 may have a total surface area of permeable membrane formed by the hollow fibers between about 4,200 square centimeters and about 18,000 square centimeters, depending on the type of HFC used. Further, the gas flow rate was varied between about 2 liters per minute to about 10 liters per minute, and the plasma flow rate was varied between about 10 mL per minute to about 60 mL per minute. Operating the once-through final subsystem 99 in this manner can reduce the initial concentrations of solvents from between about 28,000 ppm and 9,000 ppm to between about 1327 ppm and about 0.99 ppm within between about 14 minutes and 30 minutes.

2. Recirculating Solvent Removal Subsystem

In another embodiment as shown in FIG. 3, the final phase subsystem may be composed of a recirculating final phase subsystem 43 requiring that a fluid be passed multiple times through the subsystem before the residual extraction solvents have been removed to an acceptable level. Recirculating final phase subsystem 43 differs from the once-through final phase subsystem 41 in that the flow rate of the fluid in the recirculating final phase subsystem 43 is much faster than the flow rate of the fluid through the once-through final phase subsystem 41. The controlling parameters are residence time in the HFC, which is dictated by the flow rate, and interior volume of the HFC.

Recirculating final phase subsystem 43 is similar in design to the once-through final phase subsystem 41 described above. Specifically, the recirculating final phase subsystem 43 includes a re-circluating vessel 90 coupled to at least two HFCs 92 and 94 in a parallel configuration. The export ports 97 and 99 of HFCs 92 and 94 are in turn coupled to an input port 93 of recirculating vessel 90. Recirculating vessel 90 also includes a port 95 for receiving fluid from intermediate phase subsystem 29. Recirculating vessel 90 may be composed of a flexible, sterile bag, a tank or other such device. Recirculating vessel 90 is coupled to pump 96 for circulating a fluid through the subsystem 41. Valves 98 and 100 are positioned to control the flow of fluid by either causing the fluid to be recirculated around the system or to be released to output buffer 102.

Recirculating final phase subsystem 43 includes a solvent sensor 104 and a pressure sensor 106 for controlling the system. In addition, the subsystem 43 includes gas filtering loop 52, which includes a carbon bed 108, a first filter 110,

TABLE 1

| Module (Quantity) | Orientation | Phase | Lumen Flow rate (cc/min) | Air Flow (L/min) | Pressure before HFC (psig) | Pressure after HFC (psig) | Carbon (g) | Volume Treated (L) | Initial DIPE conc ppm | Final DIPE conc ppm |
|---|---|---|---|---|---|---|---|---|---|---|
| Effect of Module | | | | | | | | | | |
| Fresenius F6 (1) & F8 (1) | Horiz | $H_2O$ | 20 | 9.3 | 0.44 | −0.74 | 100 | 0.75 | 9045 | 1327 |
| Spectrum 11200 $cm^2$ (2) | Horiz | $H_2O$ | 20 | ~9 | −0.13 | −1.01 | 100 | 0.75 | 9684 | 3 |
| Celgard (1) | Vertical | $H_2O$ | 20 | 11 | −0.2 | −1.21 | 100 | 0.5 | 10518 | 0.99 |
| Spectrum 11200 $cm^2$ (2) | Horiz | Human Plasma | 20 | 9.2 | 0.91 | −0.06 | 100 | 0.75 | 12200 | 6 |
| Celgard (2) | Vertical | Human | 20 | 10.1 | −0.16 | −1.3 | 150 | 0.25 | 27822 | 9 |
| Effect of Flow Rate | | | | | | | | | | |
| Spectrum 11200 $cm^2$ (2) | Horiz | $H_2O$ | 18 | | 0.71 | −0.83 | | 0.75 | 9055 | 18 |
| Spectrum 11200 $cm^2$ (2) | Horiz | $H_2O$ | 20 | | 0.65 | −0.88 | | 0.75 | 8851 | 22 |
| Spectrum 11200 $cm^2$ (2) | Horiz | $H_2O$ | 40 | | 0.7 | −0.85 | | 0.75 | 10016 | 11 |
| Spectrum 11200 $cm^2$ (2) | Horiz | $H_2O$ | 60 | | 0.65 | −0.82 | 100 | 0.75 | 10134 | 93 |
| Celgard (1) | Vertical | $H_2O$ | 20 | 9.3 | 0.44 | −0.2 | 100 | 0.75 | 7362 | 22 |
| Celgard (1) | Vertical | $H_2O$ | 40 | 9.2 | 0.44 | −0.2 | 100 | 0.75 | 9366 | 193 |
| Effects of Pressure | | | | | | | | | | |
| Celgard (2) | Vertical | Human | 20 | 9.7 | 0.11 | −1.33 | 100 | 0.25 | 18782 | ND |
| Celgard (2) | Vertical | Human | 20 | 9.2 | −1.39 | −2.93 | 100 | 0.25 | 15246 | ND |
| Celgard (2) | Vertical | Human | 20 | 8.1 | −2.79 | −4.12 | 100 | 0.25 | 13144 | ND |
| Full Body Volume | | | | | | | | | | |
| Celgard (2) | Vertical | Human | 20 | 5.3 | −1.1 | −1.8 | 300 | 3100 | 9040 | 24 |

TABLE 2

| | DIPE concentrations [ppm] | | |
|---|---|---|---|
| Time [min] | Water | Bovine | Human (Norm) |
| 0 | 6782.094027 | 9473.974574 | 11351.10738 |
| 2 | 1716.182938 | 3012.065643 | 3868.491245 |
| 4 | 118.591244 | 485.1426701 | 636.1926821 |
| 6 | 16.36572648 | 102.9572692 | 125.8618995 |
| 8 | 5.364620368 | 36.33996072 | 60.440048 |
| 10 | 4.230662874 | 16.08489373 | 34.50180421 |
| 12 | 2.019251402 | 23.54890574 | 16.71332069 |
| 14 | 1.537721419 | 9.218693213 | 17.32898791 |
| 16 | 3.169227108 | 6.549024255 | 15.26858655 | a pump 112, and a second filter 114 for removing extraction solvent from a gas used in HFCs 92 and 94 in the same manner as described for the once-through final subsystem 41. Suitable filters may have lipophilic or hydrophilic membranes. First filter 110 and second filter 114 provide a sterile barrier between pump 112 and gas filtering loop 52 so that pump 112 may be removed from loop 52. Recirculating final phase subsystem 43 also includes a scale 116 for weighing the contents of the output buffer 102, at least two fluid level sensors 118 and 120, temperature sensors 122, 130 and 132, a fluid pressure detector 124, a current overload detector 126, an encoder 128, pressure sensors 134 and 136, a current overload detector 138 and a vent 140.

The recirculating final phase subsystem 43 operates by circulating a fluid containing lipids or lipid-containing organisms through hollow fibers of HFCs 92 and 94 and recirculation vessel 90 while a gas or mineral oil is circulated through the shell sides of HFCs 92 and 94, or vice versa. In other words, the gas can flow through the hollow fibers, and the fluid can flow through the HFC on the shell side of the hollow fibers. During this process, solvents are removed from the fluid by passing through pores 28 of the hollow fibers of HFCs 92 and 94. This process is repeated until sensor 104 detects a solvent level lower than a predetermined threshold, which may be, but is not limited to, about 10 parts per million (ppm) for n-butanol. Then valve 98 is closed, and valve 100 is opened to direct the fluid to output buffer 102. During this process, the gas that is used to remove the solvent from the fluid is sent through the carbon bed 108 to remove the solvent from the gas. The gas is processed in this manner while the fluid is circulated through HFCs 92 and 94.

HFCs 92 and 94 have been tested and successfully reduce total concentrations of solvents, such as di-isopropyl ether and di-ethyl ether, in water and plasmas, such as human and bovine plasma, as shown in Table 3 below. HFCs 92 and 94 may have a total surface area of permeable membrane formed by the hollow fibers between about 4,200 square centimeters and about 18,000 square centimeters, depending on the type of HFC used. Further, the gas flow rate was varied between about 2 liters per minute to about 14 liters per minute, and the plasma flow rate was varied between about 9 mL per minute to about 900 mL per minute. Operating the recirculating subsystem 43 in this manner can reduce the initial concentrations of solvents, such as DiPE and DEE, from between about 31,000 ppm and 9,400 ppm to between about 312 ppm and about 2 ppm within between about 14 minutes and 80 minutes.

D. Additional System Components

A solvent sensing device may be positioned within initial phase subsystem 11, intermediate phase subsystem 29, or final phase subsystem 47 to detect the presence of solvent in either the fluid and/or in the gas used in final phase subsystem 47. The fluid may be circulated through intermediate phase subsystem 29 until the solvent sensing device indicates that the solvent has been substantially removed, at which point the fluid can be used for administration to the animal or human or collected for subsequent therapeutic use.

Various types of solvent sensing devices may be used. Preferably the sensors are capable of detecting very low levels of solvent. One such sensor is capable of measuring differences in infrared absorption spectra between solvents and plasma. Using approaches known to those skilled in the art, several light sources and detectors can be integrated into a non-contact optical sensor that can be calibrated to measure the concentrations of one or all of the solvents. Another useful sensor includes a resistive sensor, such as model number TGS2620 or TGS822 available from Figaro USA Inc., Glenview, Ill., that uses a resistance processor to detect presence of very low levels of solid particles. Yet another type of optical sensor includes one that determines or identifies molecules comprising a solvent. Optionally, indirect measurement of solvent level in the fluid could be performed by measuring the amount of solvent in gas circulation loop 52. However, direct measurement is more reliable, because an obstruction in filter(s) 56, 58 or other flow impediment may falsely indicate that solvent has been extracted from the gas, when the solvent has remained in the fluid.

Suitable materials for use in any of the apparatus components as described herein include materials that are biocompatible, approved for medical applications that involve contact with internal body fluids, and in compliance with U.S. PV1 or ISO 10993 standards. Further, the materials should not substantially degrade during at least a single use, from for instance, exposure to the solvents used in the present invention. The materials should typically be sterilizable, preferably by radiation or ethylene oxide (EtO) sterilization. Such suitable materials should be capable of being formed into objects using conventional processes, such as, but not limited to, extrusion, injection molding and others. Materials meeting these requirements include, but are not limited to, nylon, polypropylene, polycarbonate, acrylic, polysulphone, polyvinylidene fluoride (PVDF), fluoroelastomers such as VITON, available from DuPont Dow Elastomers L.L.C., thermoplastic elastomers such as SANTOPRENE, available from Monsanto, polyurethane,

TABLE 3

| Lumen Material | Solvent to be Removed | Shell Material | Shell Flow | Lumen Flow | Module (Surface Area) | Initial Solvent Conc (ppm) | Final Solvent Conc (ppm) | Time recirculating |
|---|---|---|---|---|---|---|---|---|
| Water | Diethyl Ether | Air | 7 L/min | 220 | Fresenius F80A (18000 cm2) | 31000 | 265 | 30 min |
| Water | Diisopropyl Ether | Air | 12.3 L/min | 750 | Celgard (8400 cm2) | 6782 | 2 | 14 min |
| Bovine Plasma | Diisopropyl Ether | Air | 12.3 L/min | 750 | Celgard (8400 cm2) | 9473 | 7 | 16 min |
| Human Plasma | Diisopropyl Ether | Air | 12.3 L/min | 750 | Celgard (8400 cm2) | 11351 | 15 | 16 min |
| Water | Diisopropyl Ether | Heavy Mineral Oil | 10 cc/min | 4 cc/min | Spectrum (8000 cm2) | 4635 | 312 | 80 min | polyvinyl chloride (PVC), polytetrafluoroethylene (PTFE), polyphenylene ether (PFE), perfluoroalkoxy copolymer (PFA), which is available as TEFLON PFA from E.I. du Pont de Nemours and Company, and combinations thereof

E. Alternative Embodiments

Figure 6:
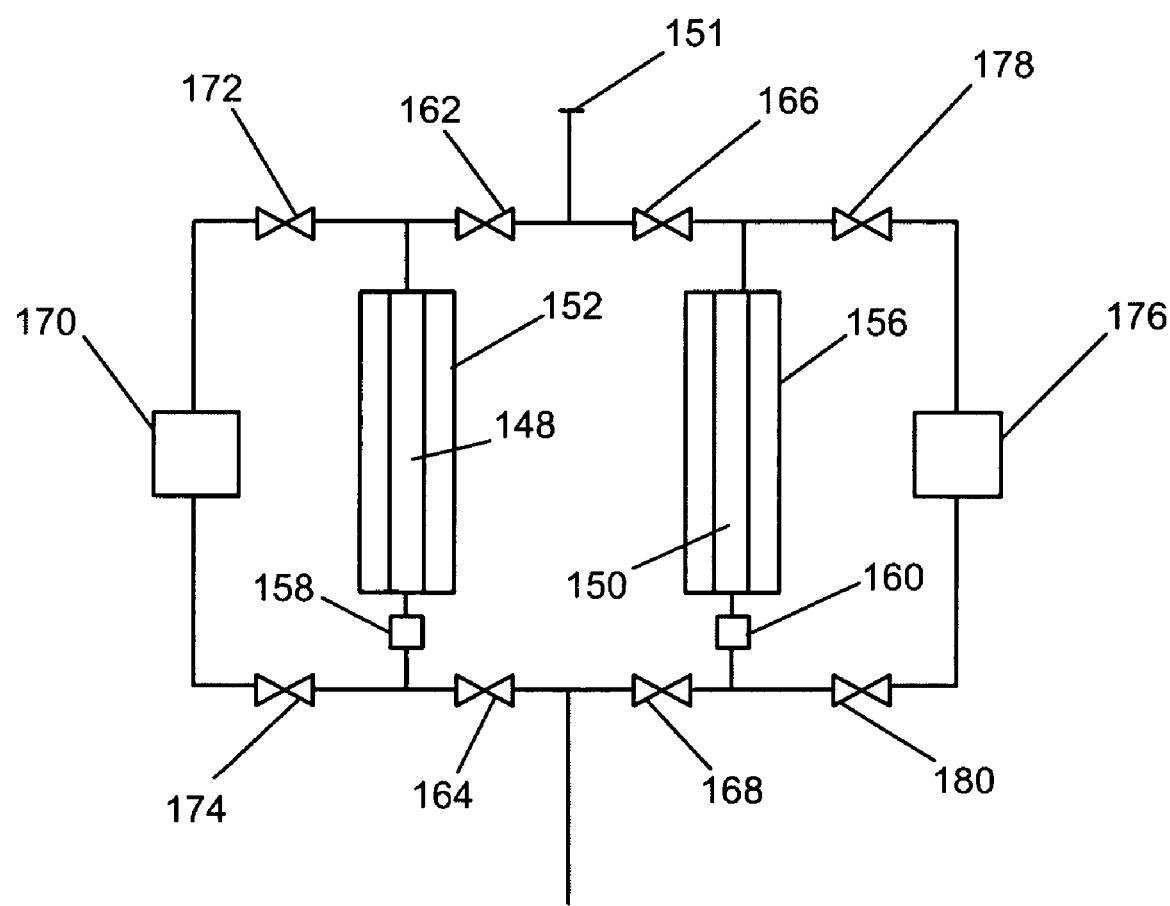
FIG. 6 depicts an alternative configuration of HFCs in the subsystems.

The embodiment described above is composed of three subsystems, wherein each subsystem includes at least one HFC. In an alternative embodiment, one or more of the subsystems can have at least two HFCs positioned in a parallel configuration, as shown schematically in FIG. 6. The parallel configuration allows a fluid to be directed through the hollow fibers 148 or 150 of HFC 152 or HFC 156. The configuration of HFC 152 and HFC 156 is not restricted to a single HFC. Rather, HFC 152 and 156 may each be composed of a plurality of HFCs connected in series. The parallel configuration of HFCs shown in FIG. 6 can be substituted for initial phase subsystem 11, intermediate phase subsystem 29, or final phase subsystem 47, or any combination of these subsystems.

The parallel configuration allows a fluid to be routed through a first side of the system until the HFC does not operate at a predetermined level because, for instance, too much lipid has attached to the inside surfaces of the hollow fibers. If this occurs, the system is reconfigured using valves 166, 168, 172 and 174 to direct the fluid through a second side of the system. While the fluid is flowing through the second side of the system, the at least one HFC in the second side can be subjected to a wash or a reverse flow, be reoriented or replaced.

The parallel configuration of the HFCs includes sensors 158 and 160 that are coupled to the lines leading to HFCs 152 and 156 to monitor the amount of lipid present in the flow coming from the hollow fibers of the HFCs. The parallel subsystem also includes valves 162, 164, 166 and 168 for controlling flow of a fluid. Initially, valves 162 and 164 are open and valves 166 and 168 are closed to direct a fluid through HFC 152, or vice versa. In operation, a fluid or a mixture of a fluid and a solvent flows through port 151 to hollow fibers 148 of HFC 152 until sensor 158 detects the presence of a lipid greater than a predetermined threshold. Upon detection of a lipid above the threshold limit, the fluid is routed through the hollow fibers 150 of HFC 156 by closing valves 162 and 164 and opening valves 166 and 168. These valves may be manually operated or operated with motors or other electrical or automatic devices.

While a fluid is routed through HFC 156, HFC 152 may be subjected to a wash in wash container 170 using valves 172 and 174 to remove lipid from the inside surfaces of the hollow fibers. For instance, hexanes may be used to dissolve lipids that have attached to surfaces of the hollow fibers. Alternatively, HFC 152 may be replaced or reoriented so that the flow of fluid through the hollow fibers is opposite the direction it flowed through previously. In yei another alternative embodiment, the system can be configured so that the flow of fluid through the hollow fibers 148 of HFC 152 can be reversed without physically moving HFC 152. HFC 156 can also be arranged in the same manners as described for HFC 152. Further, HFC 152 can be subjected to a wash in a wash container 176 using valves 178 and 180.

In yet another alternative embodiment, all three phases, the initial, intermediate and final phases, of the delipidation process may be completed using one or more HFCs in series or parallel, or any combination thereof, such as shown in final phase subsystems 43 and 41 in FIGS. 2 and 3. In one embodiment, a single HFC may be used to complete all three steps. Specifically, any of the HFCs shown in the Figures, such as the HFC shown in FIG. 4, may be used to complete the steps of mixing a fluid with a first extraction solvent that forms a first mixture of the fluid and the first extraction solvent, separating at least a portion of the first extraction solvent from the mixture using a second extraction solvent, which forms a second mixture of the fluid and the first and second extraction solvents, and removing at least a portion of the first and second extraction solvents from the second mixture to yield a delipidated fluid capable of being administered to a patient without the patient experiencing undesirable consequences.

For instance, the HFC may be composed of the Celgard G478 HFC. The single HFC performs the first step of mixing a fluid and a first extraction solvent. In one embodiment, this may be accomplished by circulating a fluid through the lumens of hollow fibers of an HFC while passing a mixture of 60% DiPE and 40% n-butanol through the shell side of the lumens of the HFC for about 20 minutes, or vice versa. This process forms a first mixture of fluid and first extraction solvent and separates lipids from the fluid or lipid-containing organisms. The fluid is then circulated through the lumens of the HFC for about 90 minutes while a second extraction solvent, referred to as a wash and composed of about 100% DiPE, is circulated through the shell side of the lumens, or vice versa. This process removes the n-butanol from the first mixture and forms a second mixture including the fluid and the first and second extraction solvent. The second mixture is then circulated through the lumens of the HFC while ambient air is passed through the HFC on the shell side of the lumens, or vice versa, until the solvents have been removed from the now delipidated fluid.

IV. Delipidation Process

The delipidation process begins by priming delipidation system 10, as shown in FIG. 2, using a saline fluid stored within saline fluid source 21. Other physiological fluids may be used; however, saline is preferable because it is isotonic with plasma. The saline fluid is inserted into delipidation system 10 in order to limit the amount of water removed from the fluid during the delipidation process, and to pre-wet the fibers of the HFCs. If the saline solution is not used, an undesirable amount of water may be extracted from the fluid. Once delipidation system 10 has been primed, saline fluid source 21 is turned off and system 10 receives fluids from fluid source 14. Fluid source 14 may store the fluids for any length of time depending upon the requirements, such as temperature, of the fluids. Optionally, fluid source 14 may be temperature controlled within a range between about 4 degrees Celsius and about 37 degrees Celsius. The fluid can be sent to HFC 16 through numerous ways, such as by using pump 17 or by allowing the biological material to flow by gravity into the hollow fibers 20 of HFC 16. Alternatively, pumps may be positioned to pull fluid through HFC 16 rather than pushing it through. As the fluid flows through HFC 16, the first extraction solvent is sent from first extraction solvent source 12 to chamber 22 of HFC 16. The first extraction solvent may be sent to HFC 16 through numerous ways similar to the methods of transporting the fluid, such as by using pump 15 or gravity flow.

The first extraction solvent is delivered from first extraction solvent source 12 to chamber 22 so that the first extraction solvent flows within chamber 22 in the same direction that the fluid flows through hollow fibers 20 of HFC 16. Circulating the first extraction solvent and the fluid in this manner causes the first extraction solvent to contact the fluid by allowing the solvent to diffuse through pores 28 of hollow fiber 20 into the fluid and the lipid to diffuse across the pores 28 of hollow fiber 20. In certain embodiments, a portion of the lipid extracted from the fluid may attach to the inside surface of hollow fibers 20. In another embodiment, first phase system 11 may be configured so that the first extraction solvent is deposited within chamber 22 of HFC 16 so that the first extraction solvent flows in a direction that is generally opposite to the direction of flow of the fluid. In one embodiment, the first extraction solvent is composed of a mixture of DiPE and n-butanol. Specifically, the mixture includes about 60% DiPE and about 40% n-butanol. However, as described above, first extraction solvent is not limited to this particular mixture and may be composed of mixtures formed by the materials in the amounts listed above.

After the first extraction solvent has flowed through chamber 22 of HFC 16, the first extraction solvent is deposited within extraction solvent waste receptacle 13. The first mixture of fluid and first extraction solvent flows from hollow fibers 20 to intermediate phase subsystem 29, and more particularly, through conduit 40, and into hollow fibers 35 of HFC 34. Intermediate phase subsystem 29 operates similarly to initial phase subsystem 11.

Intermediate phase subsystem 29 continues the delipidation process started within initial phase subsystem 11 and begins to remove the first extraction solvent from the fluid. Particularly, the first mixture of fluid and first extraction solvent flows through hollow fibers 35, 37 and 39 of HFCs 34, 36 and 38. While the mixture of first extraction solvent and fluid is located in the lumens of hollow fibers 35, 37 and 39, the second extraction solvent is transferred from second extraction solvent source 44 to chamber 74 of HFC 38. The second extraction solvent may be transferred to second extraction solvent source 44 using pump 45, allowed to flow by gravity into HFC 38, or by another means. Preferably, the second extraction fluid flows in a direction generally opposite to the direction of flow of the mixture located within hollow fibers 35, 37 and 39 of HFCs 34, 36 and 38, which is also referred to as countercurrent flow. Thus, the second extraction solvent flows first through HFC 38, then through HFC 36 and finally through HFC 34. However, in another embodiment, the second extraction solvent can flow generally opposite to the direction of the flow in the hollow fibers 35, 37 and 39 without flowing through HFCs 38, 36 and 34 in this particular order, but in another order. In yet another embodiment, the second extraction fluid can flow within chambers 70, 72 and 74 of HFCs 34, 36 and 38 in the same general direction as the direction of flow of the mixture in hollow fibers 35, 37 and 39 of HFCs 34, 36 and 38. As described above, the second extraction solvent may include any solvent that facilitates removal of the first extraction solvent. In one embodiment, the second extraction solvent is composed of DiPE.

While the mixture of the first extraction solvent and the fluid is in HFCs 34, 36 and 38, the second extraction solvent passes from chambers 70, 72, and 74 through hollow fibers 35, 37 and 39, thereby enabling the second extraction solvent to contact the first mixture of fluid and the first extraction solvent. After the second extraction solvent passes through HFCs 34, 36 and 38, the second extraction solvent is deposited within extraction solvent receptacle 13. The second extraction solvent removes at least a portion of the first extraction solvent and remaining lipids from the mixture. At least a portion of the first extraction solvent and remaining lipids pass across membrane 20 through pores 28. However, a portion of the second extraction solvent passes across membrane 20 through pores 28 into the mixture of the first extraction solvent and the fluid, thereby forming a second mixture. Further, in certain embodiments, a portion of the remaining lipids may attach to the inside surface of hollow fibers 35, 37 and 39.

The second mixture of the fluid, the first extraction solvent and the second extraction solvent is then sent to the final phase subsystem 47 for extracting the first and second extraction solvents from the mixture. In one embodiment where a once-through extraction system 41 is used, the mixture of the fluid and the first and second extraction solvents is sent from HFC 38 to hollow fibers 76 of HFC 48 through conduit 50. While the mixture flows into HFC 48, a gas is sent into chamber 80 of HFC 48 from gas filtering loop 52. In one embodiment, the gas flows in a direction generally opposite to the flow of mixture of the fluid and the first and second extraction solvents in the plurality of hollow fibers 76 and 78 of HFCs 48 and 49. However, this flow can be reversed as described above. As the gas is circulated through chambers 80 and 82 of HFCs 48 and 49, the gas fills the pores of hollow fibers 76 and 78. If a volatile solvent is used as the first extraction solvent, any gas capable of extracting the first extraction solvent from the delipidated plasma may be used such as, but not limited to, air, nitrogen or other inert gases.

The first and second extraction solvents are removed from the fluid as the gas fills pores 28 of the hollow fiber 20. The solvent diffuses through the pores 28 of the hollow fiber 20 and dissolves into the gas flowing around the fibers in chamber 22. In other words, the solvent volatilizes at hollow fiber 20. The solvent is typically highly soluble in the gas, meaning that resistance to solvent transfer is most significant at the inside wall of the hollow fiber 20. Typically, resistance to solvent transfer is a mathematical function of fluid velocity in hollow fiber 20 raised to the one third power. Many factors may be adjusted so that the fluid does not weep through fiber membrane 20, and the gas does not push through pores 28 to form a droplet phase in the fluid. Specifically, the surface chemistry and surface tension are controlled by adjusting properties of hollow fiber 20 such as pressure, temperature, fluid flow rate, material, and the like. Alternatively, these properties can be adjusted so that the fluid enters pores 28 rather than the gas. Preferably, the fibers are hydrophobic and prevent the plasma from flowing through the pores. Advantageously, hydrophobic fibers provide a more robust membrane, and the differential pressure across the wall of the fiber is not as critical. Alternatively, the fibers may be hydrophilic, as described above. During this process, the first and second extraction solvents diffuse into the gas, and the gas containing these solvents is carried from chambers 80 and 82 to gas filtering loop 52.

If the once-through final phase subsystem 41 is used, the second mixture of fluid and solvents is sent through the at least one HFC only one time. However, if the final phase subsystem is a recirculating final phase subsystem 43, the second mixture of fluid and solvents is required to be circulated multiple times through the system 43 before the solvent level within the delipidated fluid is reduced to a level enabling the delipidated fluid to be safely administered to a patient. Sensor 104 is used to detect the presence of a solvent to determine whether the final phase is complete.

In gas filtering loop 52, the gas containing the first and second extraction solvents is passed through carbon bed 54 to remove a significant portion of the solvents. The gas then flows through first filter 56 for removal of remaining first and second extraction solvents located within the gas. The gas flows through first pressure regulator 60, pump 64, and second pressure regulator 62. Any solvents are filtered out using second filter 58 before sending the gas to HFCs 48 and 49. The gas can be vented through vent 68 if desired. This process was described for gas filtering loop 52 coupled to the once-through final phase subsystem 41. However, this process is the same process used to clean the gas of solvents in the recirculating final phase subsystem 43.

V. Example

The delipidation process using an embodiment of this invention begins by first priming delipidation system 10 with about 1 liter of saline solution stored within saline fluid source 21. In addition, the shell side of the lumens of HFC 16 is primed with DiPE and n-butanol, and the shell sides of HFCs 34, 36 and 38 are primed with DiPE. Once primed, plasma is introduced to HFC 16 at a flow rate of about 20 milliliters per minute, wherein the plasma contacts a first extraction solvent composed of a premix mixture of about 60 percent di-isopropyl ether (DiPE) and about 40 percent n-butanol. The first extraction solvent flows through a HFC at a rate of about 20 milliliters per minute and in the same general direction as the plasma. The first extraction solvent and the plasma contact each other, and the first extraction solvent removes a substantial amount of lipids from the plasma. In one embodiment, the initial phase subsystem removes up to about 80 percent of total cholesterol and triglycerides and about 100 percent of HDL. HFC 16 has about 1.8 square meters of permeable surface area through which the first extraction solvent can flow and a holdup capacity of 0.1 liter. Initial phase subsystem 11 removes lipids and produces a first mixture of fluid and first extraction solvent.

The first mixture is then sent to HFC 34 in intermediate phase subsystem 29 at a rate of about 20 milliliters per minute where it is washed with a second extraction solvent composed of DiPE flowing at a rate of 40 milliliters per minute generally opposite to the direction of flow of the plasma in HFC 34. Specifically, the second extraction solvent flows through chambers 70, 72 and 74 while the first mixture of the first extraction solvent and plasma flows through the plurality of hollow fibers 35, 37 and 39 in a direction generally opposite to the second extraction solvent. While in intermediate phase subsystem 29, the plasma flows through HFCs 34, 36 and 38, which have a total permeable surface area of hollow fibers of about 3.3 square meters. These HFCs each have a holdup capacity of about 0.1 liter within the hollow fibers, totaling about 0.3 liters for the intermediate phase subsystem 29. Intermediate phase subsystem 29 produces a second mixture composed of the fluid and the first and second extraction solvents. In one embodiment, using the parameters listed above, approximately 40,000 ppm of n-butanol, and 10,000 ppm of DiPE is mixed in the plasma as the plasma enters intermediate phase subsystem 29. The second extraction solvent comprising DiPE flowing counter to the plasma at a rate of about 40 milliliter per minute lowers the n-butanol concentration from about 40,000 ppm to about 0 ppm before the plasma leaves HFC 38. Having the second extraction solvent flowing against the flow of plasma allows second extraction solvent containing 0 ppm of n-butanol to contact the plasma having little n-butanol just before it leaves HFC 38. Thus, the second extraction solvent is able to extract the lower concentration of n-butanol more easily using this configuration.

In one embodiment, the second mixture received from intermediate phase subsystem 29 is then sent to a final phase subsystem 47. The final phase subsystem may be either a once-through final phase subsystem 41 or a recirculating final phase subsystem 43. In the once-through final phase subsystem 41, the mixture of fluid and solvents is sent through pervaporation buffer source 30 where sensor 31 determines the amount of n-butanol within plasma. If the plasma contains n-butanol, the plasma is returned to HFC 34 through conduit 33. Otherwise, the delipidated plasma is sent to HFCs 48 and 49 where the first and second extraction solvents (DiPE and n-butanol) are removed by passing the delipidated plasma mixture through the hollow fibers 76 and 78 of HFCs 48 and 49 at a rate of between about 10 milliliters per minute and about 60 milliliters per minute and passing air through the chambers 80 and 82 of HFCs 48 and 49 at a flow rate varying between about 2 liters per minute to about 10 liters per minute in a direction generally opposite to the flow of the delipidated plasma mixture. Typically, the HFCs 48 and 49 include hollow fibers made of polysulfone and polypropylene fibers, such as those produced by Celgard, Charlotte, N.C., Spectrum Laboratories, Inc., Rancho Dominguez, Calif., and Fresenius, Berlin, Germany. HFCs 48 and 49 include a total surface area of permeable membrane formed by the hollow fibers between about 4,200 square centimeters and about 18,000 square centimeters depending on the type of HFC used. Operating the once-through final subsystem 41 in this manner can reduce the initial concentrations of solvents from between about 28,000 ppm (parts per million) and 9,000 ppm to between about 1327 ppm and about 0.99 ppm in about 16 minutes.

If the recirculating final phase subsystem 43 is used, the mixture of fluid and solvent is required to be sent through HFCs 92 and 94 multiple times to sufficiently reduce the level of solvents in the fluid. Typically, the HFCs 92 and 94 in the recirculating final phase subsystem 43 include polysulfone and polypropylene fibers, such as those produced by Celgard, Charlotte, N.C., Spectrum Laboratories, Inc., Rancho Dominguez, Calif., and Fresenius, Berlin, Germany. HFCs 92 and 94 each include a total surface area of permeable membrane formed by the hollow fibers between about 4,200 square centimeters and about 18,000 square centimeters depending on the type of HFC used. Further, the typical flow rate of gas on the shell side of the hollow fibers varies between about 2 liters per minute to about 14 liters per minute, and the flow rate of the fluid varies between about 9 milliliters per minute to about 900 milliliters per minute. Operating the recirculating final subsystem 43 in this manner can reduce the initial concentrations of solvents from between about 31,000 ppm and 6,700 ppm to between about 312 ppm and about 2 ppm within between about 14 minutes and about 80 minutes, respectively.

The air is passed through gas filtering loop 52 to remove the solvents. Specifically, the air is passed through carbon bed 54, first filter 56, first pressure regulator 60, pump 64 and second pressure regulator 62. The air may be vented through vent 68 if desired. This system can process approximately 3.5 liters of plasma in about 175 minutes. Once the delipidated plasma has passed through HFCs 48 and 49, the delipidated plasma may be returned to a patient or stored within delipidated fluid receptacle 66.

In one particular experiment, the amount of cholesterol was reduced from 155 milligrams per deciliter to about 35 milligrams per deciliter. Further, the amount of apolipoprotein B was reduced from about 50 milligrams per deciliter to about 28 milligrams per deciliter. However, the concentration of chloride ions and albumin remained relatively unchanged throughout the treatment process.

F. Exemplary Embodiments

The embodiments described above may be manufactured so that all components that come in contact with a fluid, containing lipids or lipid-containing organisms, or both, during operation are contained within a single module that may be disposable. To prevent the spread of diseases and for other health reasons, the delipidation system 10 should be cleaned after each use before being used with a fluid from a different source. In one embodiment, a module containing the devices described above is disposable, which enables the system to be set up quickly after having been used. Delipidation device 10 may be prepared for use with another patient's fluid by simply removing a module and replacing it with a sterile module that may have never been used or may have been sterilized since a prior use.

G. Experimental Results

A system having an initial, intermediate, and final phase subsystems was employed. The initial phase subsystem was composed of three HFCs manufactured by Celgard. The intermediate phase subsystems was composed of three HFCs manufactured by Spectrum and the final phase subsystem was composed of two HFCs manufactured by Celgard. All HFCs were oriented in series. Plasma was applied to the lumens of the HFCs. In the initial phase subsystem, the shell side of the HFCs contained a mixture of 40% butanol and 60% DIPE flowing in the same direction as the plasma flowing through the lumens of the HFCs at a rate of about 20 ml/min.

In the intermediate phase subsystem, 100 percent DiPE flowed through the HFCs on the shell side of the lumens at a rate of 40 ml per minute in a countercurrent direction to the direction of flow of the plasma through the lumens of the HFCs. In the final phase subsystem, air flowed through the three HFCs on the shell side of the lumens. Clinical chemistry data characterizing the parameters in the effluent delipidated plasma were obtained using a Hitachi 911. Results indicated dramatic reductions in cholesterol, triglycerides and HDL. Very little change or no change was observed in electrolytes (Na, Cl, and K), calcium, phosphorous, protein, albumin, globulin, phospholipids, creatinine, BUN, glucose, and alkaline phosphatase.

While various embodiments of this invention have been set forth above, these descriptions of the preferred embodiment are given for purposes of illustration and explanation. Variations, changes, modifications, and departures from the systems and methods disclosed above may be adopted without departure from the spirit and scope of this invention.

We claim:

1. A system for removing at least one lipid from a fluid containing lipids or lipid-containing organisms, comprising:
    an initial phase subsystem comprising:
        a fluid source containing the fluid and coupled to a first device that combines the fluid with a first extraction solvent;
        a first extraction solvent source containing the first extraction solvent and coupled to the first device; and
        the first device comprising at least one hollow fiber contactor, wherein the first device receives and mixes the fluid from the fluid source and the first extraction solvent from the first extraction solvent source, forming a first mixture and dissolving at least a portion of the lipids;
    an intermediate phase subsystem comprising:
        a second extraction solvent source containing a second extraction solvent and coupled to a second device that combines the first mixture with the second extraction solvent;
        the second device comprising at least one hollow fiber contactor and coupled to the first device, wherein the second device receives and mixes the first mixture from the first device and the second extraction solvent from the second extraction solvent source, forming a second mixture and dissolving additional lipids and at least a portion of the first extraction solvent;
    a final phase subsystem comprising:
        a third device comprising at least one hollow fiber contactor and coupled to the second device, wherein the third device receives the second mixture and contacts the second mixture with a gas or mineral oil, removing at least a portion of any remaining solvents from the second mixture.

2. The system of claim 1, further comprising an extraction solvent waste receptacle coupled to the first, second, and third devices.

3. The system of claim 1, wherein the initial phase subsystem further comprises a saline source coupled to the first device.

4. The system of claim 3, wherein the initial phase subsystem further comprises:
    a first pump disposed between the fluid source and the first device that transfers the fluid to the first device;
    a second pump disposed between the first extraction solvent source and the first device that transfers the first extraction solvent to the first device; and
    a third pump disposed between the saline source and the first device that transfers saline to the first device.

5. The system of claim 4, wherein the intermediate phase subsystem further comprises a fourth pump disposed between the second extraction solvent source and the second device that transfers the second extraction solvent to the second device.

6. The system of claim 1, wherein the final phase subsystem further comprises a sensor that detects levels of the first extraction solvent, the second extraction solvent, or both, the sensor coupled to a conduit disposed adjacent an exit opening of the third device.

7. The system of claim 1, wherein the final phase subsystem further comprises:
    a pervaporation buffer source coupled to a conduit that connects the second device to the third device, the pervaporation buffer source including a sensor that detects levels of the first extraction solvent, the second extraction solvent, or both within the second mixture.

8. The system of claim 1, wherein the final phase subsystem further comprises a gas filtering loop that removes the first extraction solvent and the second extraction solvent from the gas.

9. The system of claim 8, wherein the gas filtering loop further comprises:
    a carbon bed coupled to the third device such that the carbon bed receives gas having first and second extraction solvents;
    two filters and two pressure regulators disposed downstream of the carbon bed; and
    a pump that circulates gas through the gas filtering loop and the third device.

10. The system of claim 1, wherein the final phase subsystem is a recirculating system that recirculates the second mixture through the third device until solvent levels are below a predetermined threshold.

11. The system of claim 10, wherein the final phase subsystem further comprises a recirculating vessel with at least two input ports and an output port, wherein an output port of the third device is coupled to a first input port of the recirculating vessel, an output port of the second device is coupled to a second input port of the recirculating vessel, and the output port of the recirculating vessel is coupled to an input port of the third device.

12. The system of claim 11, wherein the final phase subsystem further comprises a gas filtering loop that removes the first extraction solvent and the second extraction solvent from the gas.

13. The system of claim 12, wherein the final phase subsystem further comprises a sensor that detects levels of the first extraction solvent, the second extraction solvent, or both, the sensor coupled to a conduit disposed adjacent the outlet port of the recirculating vessel.

14. The system of claim 13, wherein the final phase subsystem further comprises at least one valve that directs the second mixture from the conduit adjacent the outlet port of the recirculating vessel (i) to an output buffer when solvent levels are below the predetermined threshold or (ii) to the third device when solvent levels are above the predetermined threshold.

* * * * *